United States Patent [19]
Fowlkes

[11] Patent Number: 5,338,833
[45] Date of Patent: Aug. 16, 1994

[54] CARBOXY TERMINAL IL-6 MUTEINS

[75] Inventor: Dana M. Fowlkes, New York, N.Y.

[73] Assignee: The University of North Carolina at Chapel Hill, Chapel Hill, N.C.

[21] Appl. No.: 918,181

[22] Filed: Jul. 23, 1992

[51] Int. Cl.$^5$ .............................................. C07K 13/00
[52] U.S. Cl. .................... 530/351; 930/141
[58] Field of Search ....................... 530/351; 930/141; 435/69.52

[56] References Cited

FOREIGN PATENT DOCUMENTS

WO8800206  1/1988  World Int. Prop. O. .
WO9006370  6/1990  World Int. Prop. O. .

OTHER PUBLICATIONS

Lubeck et al., JBC 267 (21) 1992, pp. 14832–14838.
Lutticken et al., FEBS 282(2) 1991, pp. 265–267.
Fiorillo et al., Eur. J. Immunol. 22, 1992, pp. 2609–2615.
Yasueda et al., Biochem. Biophys. Res. Comm. 187(1) 1992, pp. 18–25.
Fontaine et al., Eur. J. Biochem. 211, 1993, pp. 749–755.
Nishimura et al., FEBS 311(2) 1992, pp. 271–275.
Danley et al. FEBS 283(1) 1991, pp. 135–139.
Fontaine et al. Gene 104, 1991, pp. 227–234.
Nishimura et al., Eur. J. Biochem., 196(2) 1991, pp. 377–384 (abstract only).
Sugasarawa et al., Biotechnology 6, 895–902 (1988).
Lokker et al., Embo J., 10 (8), 2125–2131 (1991).
Bazan, J. F. Immunol. Today 11, 350–354 (1990).
Brakenhoff et al., Journal of Immunology 143, 1175–1182 (1989).
Kruttgen, Al., et al., FEBS. Lett. 273, 95–98 (1990).
Snouwaert, J. N., et al., Journal of Biological Chemistry 266 (34) 23097–23102 (1991).

*Primary Examiner*—Garnette D. Draper
*Attorney, Agent, or Firm*—Irving N. Feit; Eric J. Sheets; Laura S. Weiss

[57] ABSTRACT

This invention relates to a Carboxy Terminal IL-6 Mutein with enhanced biological activity. The invention comprises a mutein of IL-6 having increased activity wherein the mutein has an amino acid substitution at, or corresponding to, amino acid location 171 or 175 of IL-6 having the wild-type sequence.

15 Claims, 6 Drawing Sheets

```
GCT CCG GTT CCG CCA GGA GAA GAT TCC AAA GAT GTA GCC GCC CCA CAC    048
Ala Pro Val Pro Pro Gly Glu Asp Ser Lys Asp Val Ala Ala Pro His
 1            5                  10                  15

AGA CAG CCG CTC ACC TCT TCA GAA CGA ATC GAT AAA CAA ATT CGG TAC    096
Arg Gln Pro Leu Thr Ser Ser Glu Arg Ile Asp Lys Gln Ile Arg Tyr
               20                  25                  30

ATC CTC GAC GGG ATA TCA GCG CTG AGA AAA GAG ACC TGT AAC AAG AGT    144
Ile Leu Asp Gly Ile Ser Ala Leu Arg Lys Glu Thr Cys Asn Lys Ser
            35                  40                  45

AAC ATG TGT GAA AGC AGT AAA GAA GCA CTG GCA GAA AAC AAC CTG AAC    192
Asn Met Cys Glu Ser Ser Lys Glu Ala Leu Ala Glu Asn Asn Leu Asn
         50                  55                  60

CTT CCG AAG ATG GCT GAA AAA GAT GGA TGT TTT CAA TCT GGA TTC AAT    240
Leu Pro Lys Met Ala Glu Lys Asp Gly Cys Phe Gln Ser Gly Phe Asn
 65               70                  75                  80

GAG GAA ACT TGT CTG GTG AAA ATC ATC ACA GGC CTT TTG GAA TTT GAG    288
Glu Glu Thr Cys Leu Val Lys Ile Ile Thr Gly Leu Leu Glu Phe Glu
                  85                  90                  95

GTA TAC CTA GAG TAC CTC CAG AAC AGA TTT GAG AGT AGT GAG GAA CAA    336
Val Tyr Leu Glu Tyr Leu Gln Asn Arg Phe Glu Ser Ser Glu Glu Gln
               100                 105                 110

GCG AGA GCT GTC CAG ATG TCG ACC AAA GTC CTG ATC CAG TTT CTG CAG    384
Ala Arg Ala Val Gln Met Ser Thr Lys Val Leu Ile Gln Phe Leu Gln
            115                 120                 125

AAA AAG GCA AAA AAT CTA GAT GCA ATA ACC ACC CCG GAT CCA ACC ACA    432
Lys Lys Ala Lys Asn Leu Asp Ala Ile Thr Thr Pro Asp Pro Thr Thr
 130                 135                 140

AAT GCG AGC CTG CTG ACG AAG CTG CAG GCA CAG AAC CAG TGG CTG CAG    480
Asn Ala Ser Leu Leu Thr Lys Leu Gln Ala Gln Asn Gln Trp Leu Gln
145               150                 155                 160

GAC ATG ACA ACT CAT CTC ATT CTG AGA TCT TTG AAA GAA TTC ATG CAG    528
Asp Met Thr Thr His Leu Ile Leu Arg Ser Leu Lys Glu Phe Met Gln
               165                 170                 175

TCC TCC CTG CGT GCT CTG CGT CAG ATG TAATGATAG                       564
Ser Ser Leu Arg Ala Leu Arg Gln Met
            180                 185
```

Figure 1.

| | | | | | | | | | | | | | | | | |
|---|---|---|---|---|---|---|---|---|---|---|---|---|---|---|---|---|
| GCT | CCG | GTT | CCG | CCA | GGA | GAA | GAT | TCC | AAA | GAT | GTA | GCC | GCC | CCA | CAC | 048 |
| Ala | Pro | Val | Pro | Pro | Gly | Glu | Asp | Ser | Lys | Asp | Val | Ala | Ala | Pro | His | |
| 1 | | | | 5 | | | | | 10 | | | | | 15 | | |

AGA CAG CCG CTC ACC TCT TCA GAA CGA ATC GAT AAA CAA ATT CGG TAC    096
Arg Gln Pro Leu Thr Ser Ser Glu Arg Ile Asp Lys Gln Ile Arg Tyr
         20                  25                  30

ATC CTC GAC GGG ATA TCA GCG CTG AGA AAA GAG ACC TGT AAC AAG AGT    144
Ile Leu Asp Gly Ile Ser Ala Leu Arg Lys Glu Thr Cys Asn Lys Ser
             35                  40                  45

AAC ATG TGT GAA AGC AGT AAA GAA GCA CTG GCA GAA AAC AAC CTG AAC    192
Asn Met Cys Glu Ser Ser Lys Glu Ala Leu Ala Glu Asn Asn Leu Asn
     50                  55                  60

CTT CCG AAG ATG GCT GAA AAA GAT GGA TGT TTT CAA TCT GGA TTC AAT    240
Leu Pro Lys Met Ala Glu Lys Asp Gly Cys Phe Gln Ser Gly Phe Asn
 65                  70                  75                  80

GAG GAA ACT TGT CTG GTG AAA ATC ATC ACA GGC CTT TTG GAA TTT GAG    288
Glu Glu Thr Cys Leu Val Lys Ile Ile Thr Gly Leu Leu Glu Phe Glu
                 85                  90                  95

GTA TAC CTA GAG TAC CTC CAG AAC AGA TTT GAG AGT AGT GAG GAA CAA    336
Val Tyr Leu Glu Tyr Leu Gln Asn Arg Phe Glu Ser Ser Glu Glu Gln
             100                 105                 110

GCG AGA GCT GTC CAG ATG TCG ACC AAA GTC CTG ATC CAG TTT CTG CAG    384
Ala Arg Ala Val Gln Met Ser Thr Lys Val Leu Ile Gln Phe Leu Gln
         115                 120                 125

AAA AAG GCA AAA AAT CTA GAT GCA ATA ACC ACC CCG GAT CCA ACC ACA    432
Lys Lys Ala Lys Asn Leu Asp Ala Ile Thr Thr Pro Asp Pro Thr Thr
 130                 135                 140

AAT GCG AGC CTG CTG ACG AAG CTG CAG GCA CAG AAC CAG TGG CTG CAG    480
Asn Ala Ser Leu Leu Thr Lys Leu Gln Ala Gln Asn Gln Trp Leu Gln
145                 150                 155                 160

GAC ATG ACA ACT CAT CTC ATT CTG AGA TCT TTT AAA GAA TTC CTG CAG    528
Asp Met Thr Thr His Leu Ile Leu Arg Ser Phe Lys Glu Phe Leu Gln
             165                 170                 175

TCC TCC CTG CGT GCT CTG CGT CAG ATG TAATGATAG                      564
Ser Ser Leu Arg Ala Leu Arg Gln Met
         180                 185

Figure 2.

```
GCT CCG GTT CCG CCA GGA GAA GAT TCC AAA GAT GTA GCC GCC CCA CAC    048
Ala Pro Val Pro Pro Gly Glu Asp Ser Lys Asp Val Ala Ala Pro His
 1           5                   10                  15

AGA CAG CCG CTC ACC TCT TCA GAA CGA ATC GAT AAA CAA ATT CGG TAC    096
Arg Gln Pro Leu Thr Ser Ser Glu Arg Ile Asp Lys Gln Ile Arg Tyr
             20                  25                  30

ATC CTC GAC GGG ATA TCA GCG CTG AGA AAA GAG ACC TGT AAC AAG AGT    144
Ile Leu Asp Gly Ile Ser Ala Leu Arg Lys Glu Thr Cys Asn Lys Ser
         35                  40                  45

AAC ATG TGT GAA AGC AGT AAA GAA GCA CTG GCA GAA AAC AAC CTG AAC    192
Asn Met Cys Glu Ser Ser Lys Glu Ala Leu Ala Glu Asn Asn Leu Asn
     50                  55                  60

CTT CCG AAG ATG GCT GAA AAA GAT GGA TGT TTT CAA TCT GGA TTC AAT    240
Leu Pro Lys Met Ala Glu Lys Asp Gly Cys Phe Gln Ser Gly Phe Asn
 65              70                  75                  80

GAG GAA ACT TGT CTG GTG AAA ATC ATC ACA GGC CTT TTG GAA TTT GAG    288
Glu Glu Thr Cys Leu Val Lys Ile Ile Thr Gly Leu Leu Glu Phe Glu
                 85                  90                  95

GTA TAC CTA GAG TAC CTC CAG AAC AGA TTT GAG AGT AGT GAG GAA CAA    336
Val Tyr Leu Glu Tyr Leu Gln Asn Arg Phe Glu Ser Ser Glu Glu Gln
             100                 105                 110

GCG AGA GCT GTC CAG ATG TCG ACC AAA GTC CTG ATC CAG TTT CTG CAG    384
Ala Arg Ala Val Gln Met Ser Thr Lys Val Leu Ile Gln Phe Leu Gln
         115                 120                 125

AAA AAG GCA AAA AAT CTA GAT GCA ATA ACC ACC CCG GAT CCA ACC ACA    432
Lys Lys Ala Lys Asn Leu Asp Ala Ile Thr Thr Pro Asp Pro Thr Thr
     130                 135                 140

AAT GCG AGC CTG CTG ACG AAG CTG CAG GCA CAG AAC CAG TGG CTG CAG    480
Asn Ala Ser Leu Leu Thr Lys Leu Gln Ala Gln Asn Gln Trp Leu Gln
145                 150                 155                 160

GAC ATG ACA ACT CAT CTC ATT CTG AGA TCT TTG AAA GAA TTC CTG CAG    528
Asp Met Thr Thr His Leu Ile Leu Arg Ser Leu Lys Glu Phe Leu Gln
                 165                 170                 175

TCC TCC CTG CGT GCT CTG CGT CAG ATG TAATGATAG                      564
Ser Ser Leu Arg Ala Leu Arg Gln Met
             180                 185
```

Figure 3.

```
GCT CCG GTT CCG CCA GGA GAA GAT TCC AAA GAT GTA GCC GCC CCA CAC    048
Ala Pro Val Pro Pro Gly Glu Asp Ser Lys Asp Val Ala Ala Pro His
 1           5                  10                  15

AGA CAG CCG CTC ACC TCT TCA GAA CGA ATC GAT AAA CAA ATT CGG TAC    096
Arg Gln Pro Leu Thr Ser Ser Glu Arg Ile Asp Lys Gln Ile Arg Tyr
             20                  25                  30

ATC CTC GAC GGG ATA TCA GCG CTG AGA AAA GAG ACC TGT AAC AAG AGT    144
Ile Leu Asp Gly Ile Ser Ala Leu Arg Lys Glu Thr Cys Asn Lys Ser
             35                  40                  45

AAC ATG TGT GAA AGC AGT AAA GAA GCA CTG GCA GAA AAC AAC CTG AAC    192
Asn Met Cys Glu Ser Ser Lys Glu Ala Leu Ala Glu Asn Asn Leu Asn
     50                  55                  60

CTT CCG AAG ATG GCT GAA AAA GAT GGA TGT TTT CAA TCT GGA TTC AAT    240
Leu Pro Lys Met Ala Glu Lys Asp Gly Cys Phe Gln Ser Gly Phe Asn
 65              70                  75                  80

GAG GAA ACT TGT CTG GTG AAA ATC ATC ACA GGC CTT TTG GAA TTT GAG    288
Glu Glu Thr Cys Leu Val Lys Ile Ile Thr Gly Leu Leu Glu Phe Glu
                 85                  90                  95

GTA TAC CTA GAG TAC CTC CAG AAC AGA TTT GAG AGT AGT GAG GAA CAA    336
Val Tyr Leu Glu Tyr Leu Gln Asn Arg Phe Glu Ser Ser Glu Glu Gln
                100                 105                 110

GCG AGA GCT GTC CAG ATG TCG ACC AAA GTC CTG ATC CAG TTT CTG CAG    384
Ala Arg Ala Val Gln Met Ser Thr Lys Val Leu Ile Gln Phe Leu Gln
        115                 120                 125

AAA AAG GCA AAA AAT CTA GAT GCA ATA ACC ACC CCG GAT CCA ACC ACA    432
Lys Lys Ala Lys Asn Leu Asp Ala Ile Thr Thr Pro Asp Pro Thr Thr
    130                 135                 140

AAT GCG AGC CTG CTG ACG AAG CTG CAG GCA CAG AAC CAG TGG CTG CAG    480
Asn Ala Ser Leu Leu Thr Lys Leu Gln Ala Gln Asn Gln Trp Leu Gln
145                 150                 155                 160

GAC ATG ACA ACT CAT CTC ATT CTG AGA TCT TTT AAA GAA TTC ATG CAG    528
Asp Met Thr Thr His Leu Ile Leu Arg Ser Phe Lys Glu Phe Met Gln
                165                 170                 175

TCC TCC CTG CGT GCT CTG CGT CAG ATG TAATGATAG                      564
Ser Ser Leu Arg Ala Leu Arg Gln Met
            180                 185
```

Figure 4.

```
GCT CCG GTT CCG CCA GGA GAA GAT TCC AAA GAT GTA GCC GCC CCA CAC    048
Ala Pro Val Pro Pro Gly Glu Asp Ser Lys Asp Val Ala Ala Pro His
 1           5                   10                  15

AGA CAG CCG CTC ACC TCT TCA GAA CGA ATC GAT AAA CAA ATT CGG TAC    096
Arg Gln Pro Leu Thr Ser Ser Glu Arg Ile Asp Lys Gln Ile Arg Tyr
             20                  25                  30

ATC CTC GAC GGG ATA TCA GCG CTG AGA AAA GAG ACC TGT AAC AAG AGT    144
Ile Leu Asp Gly Ile Ser Ala Leu Arg Lys Glu Thr Cys Asn Lys Ser
             35                  40                  45

AAC ATG TGT GAA AGC AGT AAA GAA GCA CTG GCA GAA AAC AAC CTG AAC    192
Asn Met Cys Glu Ser Ser Lys Glu Ala Leu Ala Glu Asn Asn Leu Asn
         50                  55                  60

CTT CCG AAG ATG GCT GAA AAA GAT GGA TGT TTT CAA TCT GGA TTC AAT    240
Leu Pro Lys Met Ala Glu Lys Asp Gly Cys Phe Gln Ser Gly Phe Asn
 65                  70                  75                  80

GAG GAA ACT TGT CTG GTG AAA ATC ATC ACA GGC CTT TTG GAA TTT GAG    288
Glu Glu Thr Cys Leu Val Lys Ile Ile Thr Gly Leu Leu Glu Phe Glu
                 85                  90                  95

GTA TAC CTA GAG TAC CTC CAG AAC AGA TTT GAG AGT AGT GAG GAA CAA    336
Val Tyr Leu Glu Tyr Leu Gln Asn Arg Phe Glu Ser Ser Glu Glu Gln
            100                 105                 110

GCG AGA GCT GTC CAG ATG TCG ACC AAA GTC CTG ATC CAG TTT CTG CAG    384
Ala Arg Ala Val Gln Met Ser Thr Lys Val Leu Ile Gln Phe Leu Gln
        115                 120                 125

AAA AAG GCA AAA AAT CTA GAT GCA ATA ACC ACC CCG GAT CCA ACC ACA    432
Lys Lys Ala Lys Asn Leu Asp Ala Ile Thr Thr Pro Asp Pro Thr Thr
    130                 135                 140

AAT GCG AGC CTG CTG ACG AAG CTG CAG GCA CAG AAC CAG TGG CTG CAG    480
Asn Ala Ser Leu Leu Thr Lys Leu Gln Ala Gln Asn Gln Trp Leu Gln
145                 150                 155                 160

GAC ATG ACA ACT CAT CTC ATT CTG AGA TCT TTG AAA GAA TTC ATG CAG    528
Asp Met Thr Thr His Leu Ile Leu Arg Ser Leu Lys Glu Phe Met Gln
                165                 170                 175

TCC TCC CTG CGT GCT CTG CGT CAG ATG TAATGATAG                      564
Ser Ser Leu Arg Ala Leu Arg Gln Met
            180                 185
```

Figure 5.
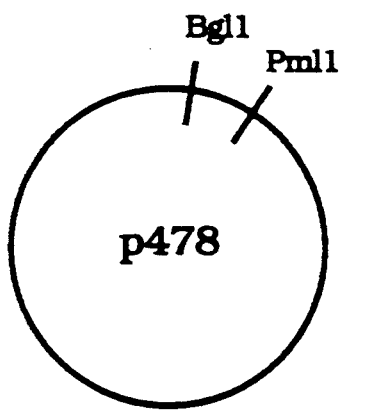
p478
Blue Phenotype
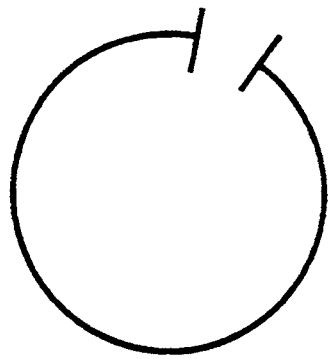
Remove
Bgl1-Pml1 Frag.
Insert 29 bp fragment
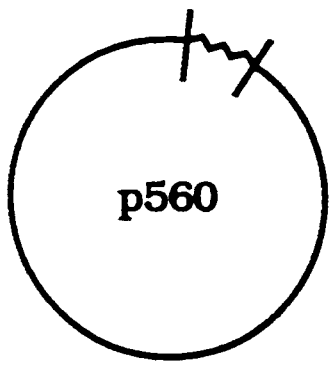
p560
White Phenotype
Remove 29 bp frag.
Insert 129 bp frag.
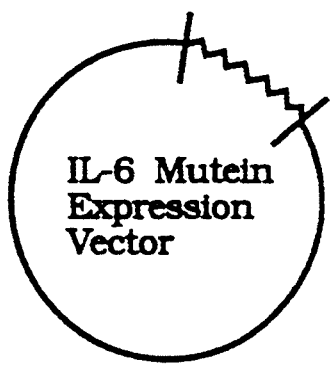
IL-6 Mutein
Expression
Vector
Blue Phenotype

Figure 6

Percentage of wild-type Interleukin-6

Legend: ■ BIOLOGICAL ACTIVITY; □ RECEPTOR BINDING CAPACITY

Sequences (positions 171–185):
- FKDFLQSSLRALRQM
- CKEFLQSSLRALRQM
- LKEFLQSSLRALRQM
- FQEFLQSSLRALRQM
- FKDFLQSSLRALRQM
- FKEVLQSSLRALRQM (N.D.)
- FKEFMQSSLRALRQM
- FKEFLKSSLRALRQM (N.D.)
- FKEFLQPSLRALRQM
- FKEFLQSRLRALRQM
- FKEFLQSSRRALRQM
- FKEFLQSSLKALRQM
- FKEFLQSSLRDLRQM
- FKEFLQSSLRTLRQM
- FKEFLQSSLRAVRQM
- FKEFLQSSLRAIRQM
- FKEFLQSSLRALWQM
- FKEFLQSSLRALRPM (N.D.)
- FKEFLQSSLRALRQI (N.D.)

CARBOXY TERMINAL IL-6 MUTEINS

BACKGROUND OF THE INVENTION

The present invention is directed to a mutein of Interleukin-6, its production by recombinant DNA technology, and its theraputic use.

Interleukin-6 (IL-6) is a multifunctional cytokine that is produced by a variety of cells such as B-cells, T-cells, monocytes, fibroblasts and endothelial cells. IL-6 exhibits several activities relating to the proliferation and/or differentiation of hematopoietic progenitor cells. These activities result from IL-6 acting alone or in combination with other cytokines such as IL-3 and IL-4. Some specific biological effects of IL-6 include terminal differentiation of B-cells, proliferation and differentiation of T-cells, regulation of the acute phase response, growth regulation of epithelial cells, the differentiation of megakaryocytes, and thrombopoiesis. In accordance with these activities and effects, the target cells for IL-6 include B-cells, T-cells, myeloma cells, megakaryocytes, monocytes, early stem cells and hepatocytes.

Though IL-6 is a multifunctional cytokine, the various biological effects it exerts are believed to be initiated by the stepwise interaction of IL-6 with two distinct receptor subunits on a cell. IL-6 first forms a complex with an 80 kD receptor subunit. This complex binds to a non-ligand subunit, which is a membrane glycoprotein designated gp130. The binding of the IL-6-80kD receptor complex to gp130 results in signal transduction.

The amino acid sequence of IL-6 has been described in the literature as containing 185 amino acids starting with alanine as residue 1; see, for example, FIG. 2A of Brakenhoff et al., *J. Immunol.* 139, 4116–4121 (1987) and FIG. 1 of Clark et al., PCT application WO 88/00206. These references also contain the cDNA sequence that corresponds to native IL-6 mRNA.

The carboxy terminus of IL-6 has been found to be the receptor binding region. (See Leebeek, F. W. G., et al., "Identification of a Receptor Binding Site in the Carboxyl Terminus of Human Interleukin-6", *Journal of Biological Chemistry*, 267, 14832–14838 (1992) Analysis of the structure of the carboxy terminal region of several cytokines, including IL-6, has shown the binding region to be highly conserved. Lokker, N., et al., EMBO J., 10, (8) 2125–2131 (1991). See page 2130, top of col. 1.; BAZAN, *Immunology Today* 11, 350–354 (1990). According to Lokker et al., "[S]ubstitutions in the . . . C-terminal proximal regions of these molecules abolished their activity."

New techniques in molecular biology, such as recombinant DNA and monoclonal antibodies, make it possible not only to study the relationships between the structure and function of proteins, but also to enable the production of protein analogs with superior properties. The analogs may differ from native proteins by deletion, substitution, or addition of amino acids to the native sequence. Since the DNA and amino acid sequences of IL-6 are known, these techniques can be used to study and improve the various properties of IL-6.

For example, the deletion of amino acids may give important information about the function of a protein. Thus, Brakenhoff et al. have reported that the biological activity of IL-6 is not affected by deletion of up to 28 amino acid residues from the amino terminus (N-terminus) of mature, native IL-6. Brakenhoff, J. P. J., et al., *J. Immunol.* 43, 1175–1182 (1989).

Conversely, deletion of only a few amino acids from the carboxy terminus (C-terminus) of IL-6 has a pronounced effect on biological activity. For example, Krüttgen et al. found that a deletion of the last amino acid from the carboxy terminus of IL-6 resulted in a fivefold loss of biological activity. Furthermore, IL-6 lacking three or four carboxy terminal amino acids was found to be completely inactive. Krüttgen, A-, et al., *FEBS Lett.* 273, 95–98 (1990).

Since these truncated forms of IL-6 were not tested for binding to the IL-6 receptor, it remains unclear whether the loss of activity observed was due to a loss of receptor binding or to a defective signal transduction upon IL-6 receptor interaction. In any event, the importance of the presence of the C-terminal amino acid residues is consistent with the highly conserved nature of this region, see above.

Additional information about the importance of the carboxy terminus of IL-6 for biological activity was obtained by Brakenhoff et al. These authors showed by epitope mapping that neutralizing monoclonal antibodies against IL-6 were directed to a region of the carboxy terminus. Brakenhoff, J. P. J., et al., *J. Immunol.* 145, 561–568 (1990).

Native proteins may be improved by substituting amino acids for one or more of the amino acids that occur naturally in a protein. Such substitutions may be introduced into a protein by expressing recombinant DNA having a nucleotide sequence modified so as to have a codon that represents the desired amino acid. Proteins expressed by such modified DNA are called muteins. The DNA may conveniently be modified using the technique of saturation mutagenesis. Hutchinson, C. A., et al., *Proc. Natl. Acad. Sci., U.S.A.* 83, 710–714 (1986).

In a typical example of a mutein, native cysteine residues are replaced by other amino acid residues. Substituting other residues for cysteine residues may make it easier to express proteins in bacteria. Snouwaert, J., et al., *J. Immunol.* 146, 585–591 (1991); See page 589, col. 1, last paragraph bridging col 2, through first full paragraph.

Muteins of IL-6 with improved biological activity relative to native IL-6 are desirable. An IL-6 mutein with enhanced biological activity would permit a lower dosage of the mutein to be administered to patients. Therefore, the costs of treatment and manufacture would be decreased with the more active IL-6 mutein. In addition, a lower dosage of the more active IL-6 mutein may reduce or eliminate possible side effects of the medication.

It is the principal objective of the present invention to produce IL-6 muteins that have amino acid substitutions such that an increase in biological activity is achieved.

Other objectives are to produce DNA, vectors and plasmids that encode muteins of IL-6 with increased activity.

SUMMARY OF THE INVENTION

These and other objectives, as will become apparent to those with skill in the art, have been met by providing a mutein of IL-6 having increased activity wherein the Phenylalanine residue at or corresponding to position 171 of the native IL-6 sequence (Phe[171]) is replaced by a Leucine (Leu) residue and/or the Leucine residue at or corresponding to position 175 of the native IL-6 sequence (Leu$^{175}$) is replaced by a Methionine (Met) residue.

DESCRIPTION OF THE SEQ. ID NOS. AND DRAWINGS

FIG. 1 shows the 185 nucleic and amino acid sequence of a full length wild-type IL-6 starting with alanine as residue 1. The underlined codons represent the sites of mutagenesis which result in the amino acid substitutions of the present invention. See SEQ. ID. NOS. 1-2.

FIG. 2 shows the 185 nucleic and amino acid sequence of a full length mutein of human IL-6 starting with alanine as residue 1. The underlined codon represents a mutation wherein the phenylalanine residue at position 171 of wild-type IL-6 is substituted by leucine. See Example 1 and SEQ. ID. NOS. 3-4.

FIG. 3 shows the 185 nucleic and amino acid sequence of a full length mutein of human IL-6 starting with alanine as residue 1. The underlined codon represents a mutation wherein the leucine residue at position 175 of wild-type IL-6 is substituted by methionine. See Example 1 and SEQ. ID. NOS. 5-6.

FIG. 4 shows the 185 nucleic and amino acid sequence of a full length mutein of human IL-6 starting with alanine as residue 1. The underlined codons represent mutations wherein the phenylalanine residue at position 171 of wild-type IL-6 is substituted by leucine and the leucine residue at position 175 of wild-type IL-6 is substituted with methionine. See Example 1 and SEQ. ID. NOS. 7-8.

FIG. 5 shows the cloning strategy for the construction of the p560 expression vector used to introduce the C-terminal amino acid substitutions of the present invention into IL-6.

FIG. 6 is a table showing the biological activity and receptor binding capacity of nineteen C-terminal IL-6 muteins with single amino acid substitutions at positions 171 through 185 of the wildtype sequence. (See Examples 3 and 4) The bar graph results of the IL-6 muteins of the present invention are located third and seventh from the top of the table. Biological activity was determined by the hepatocyte stimulation assay using human hepatoma cell line HEP3B2 as described in Example 3 See SEQ. ID NOS. 17-35.

DETAILED DESCRIPTION OF THE INVENTION

Definitions

The present invention is directed to muteins of IL-6 that have enhanced biological activity compared to that of native IL-6. It has now been unexpectedly discovered that certain mutations in the highly conserved carboxy terminal region of IL-6 result in increased biological activity. The mutations are amino acid substitutions.

In this specification, IL-6 refers to human IL-6, and includes proteins described in the literature as having the same name as IL-6. Such proteins include interferon-$\beta$-2 (IFN-$\beta$-2), B-cell stimulation factor-2 (BSF-2), B-cell hybridoma/plasmacytoma growth factor (HPGF or HGF), 26 kDa protein and hepatocyte stimulating factor (HSF). The sequence of native human IL-6 has been discussed above in the Background Section of this specification.

The words "amino acid" in this specification are understood to mean the approximately 21 naturally occurring $\alpha$-amino acids or their analogs.

The term "mutein" in this specification is understood to mean a protein that has been modified at specific amino acid locations. The modifications in the mutein of the present invention are amino acid substitutions in the carboxy terminal region of IL-6.

The muteins of the present invention are preferably essentially pure. Essentially pure means that the mutein is at least 85%, preferably at least 95% and more preferably, at least 98% free from other proteins and purification reagents.

The muteins of the present invention exhibit increased biological activity in mammals when compared with wild-type IL-6. The increased activity of the muteins may be in vitro activity, in vivo activity, or both.

The biological activity of wild-type IL-6 and IL-6 muteins can be measured by standard assays for measuring IL-6 activity, as is known in the art. For example, the in vitro biological activity of the IL-6 muteins of the invention may be compared with native IL-6 in a fibrinogen induction assay using a human hepatoma cell line, HEP3B2. When determined in such an assay and expressed as a percentage of activity of native, wild-type, IL-6, the activity of which is defined as 100%, the biological activity of the muteins of the present invention is at least 125%, preferably at least 150%. (See Example 3 and FIG. 6)

Two IL-6 muteins, each with a single point mutation, have been found to exhibit increased biological activity. A mutein containing both point mutations is also within the scope of the present invention.

An IL-6 mutein with Phenylalanine at position 171 of the native sequence (Phe$^{171}$) replaced by Leucine (Leu) has higher biological activity, such as in vitro activity on a human hepatoma cell line, compared to wild-type IL-6. The increased activity of this mutein is associated with increased receptor binding capacity.

An IL-6 mutein with Leucine at position 175 of the native sequence (Leu175) replaced by Methionine (Met) has higher biological activity, such as in vitro activity on a human hepatoma cell line, compared to wild-type IL-6. The increased activity of this mutein is associated with decreased receptor binding capacity.

A third IL-6 mutein contains mutations at both positions 171 (Phe→Leu) and 175 (Leu→Met).

The increased biological activity of the muteins of the invention may be associated with increased binding capacity or with decreased binding capacity. Binding capacity is measured in terms of the affinity of an IL-6 receptor for wild-type IL-6 or the IL-6 muteins of the invention. The affinity may be determined with a Scatchard analysis and quantitated as a dissociation constant, $K_d$. (See Leebeek, F. W. G., et al., "Identification of a Receptor Binding Site in the Carboxyl Terminus of Human Interleukin-6", *Journal of Biological Chemistry*, in press) The binding capacity of the muteins of the invention is expressed as a percentage of the binding capacity of wild-type IL-6. The percentage is calculated by dividing the dissociation constant of wild-type IL-6 by the dissociation constant of an IL-6 mutein.

The muteins of the present invention may contain all 185 amino acid residues corresponding to full length wild-type IL-6, as shown in FIG. 1 and SEQ. ID. NOS. 1 and 2. Alternatively, from 1 to 28 amino terminal (N-terminal) amino acid residues may be deleted. For example, copending commonly owned patent application U.S. Ser. No. 07/724,698 now abandoned discloses deletion of 22 N-terminal amino acids from native wild-type IL-6.

In the present invention, IL-6 F-L$^{171}$ represents the mutein containing the substitution of Phenylalanine by Leucine at position 171. See FIG. 2 and SEQ. ID. NOS. 3 and 4.

IL-6 L-M175 represents the mutein containing the substitution of Leucine by Methionine at position 175. See FIG. 3 and SEQ. ID. NOS. 5 and 6.

Where the two amino acid substitutions occur in the same mutein, the mutein will be designated IL-6 F-L$^{171}$/L-M$^{175}$. See FIG. 4 and SEQ. ID. NOS. 7 and 8.

An N-terminal deleted form of the muteins of the invention will be designated -naa IL-6 F-L$^{171}$ or -naa IL-6 L-M$^{175}$. The letter n represents the number of missing amino acid residues from the amino terminus. The single letter amino acid code is used to represent the amino acid substitutions corresponding to the positions previously described.

Thus, a mutein with the F-L$^{171}$ substitution having the first 22 N-terminal amino acids truncated is designated -22aa IL-6 F-L$^{171}$. A mutein with the L-M$^{175}$ substitution having the first 22 N-terminal amino acids truncated is designated -22aa IL-6 L-M$^{175}$. Where the two amino acid substitutions occur in the same mutein of the invention, the truncated form will be designated -naa IL-6 F-L$^{175}$, i.e. -22aa IL-6 F-L$^{171}$/L-M$^{175}$.

Native IL-6 contains four cysteine residues, which occur at positions 45, 51, 74 and 84 of the mature, full length sequence. These positions are based on the definition in this specification that the mature, native, full length IL-6 contains 185 amino acids starting with alanine as residue 1. The cysteine residues at, or that correspond to, positions 45 and 51 of native IL-6 may be replaced by other amino acids without losing significant activity. The cysteine residues at, or that correspond to position 74 and 84 of native IL-6 must be retained. (See copending patent application U.S. Ser. No. 07/724,698)

In this specification, a mutein of IL-6 that contains cysteine residues at positions 74 and 84, but not at positions 45 and 51, is called IL-6 XX$^{45,51}$ wherein X represents any naturally occurring α-amino acid or an amino acid analogue. Preferably, X represents a neutral amino acid, such as alanine, serine, threonine, proline and glycine. Preferred amino acids for replacing the cysteine residues are serine and alanine.

The two amino acids that replace the cysteine residues at positions corresponding to 45 and 51 of native, mature IL-6 (XX) may be the same or different. Some examples of XX include SS, AA, GG, DR, RD, SA, AS, etc.

An amino acid deleted form of the muteins of the present invention that also has the first two cysteines residues substituted will be designated -naa IL-6 XX, wherein X and n are as defined above. Thus, some truncated muteins lacking the N-terminal 22 amino acids are designated -22aa IL-6 XX$^{45,51}$/F-L$^{171}$; -22aa IL-6 XX$^{45,51}$/L-M$^{175}$; and -22aa IL-6 XX$^{45,51}$/F-L$^{171}$/L-M$^{175}$.

The alanine at position 1 and the alanine-proline at positions 1 and 2 of mature, full length IL-6 are sometimes cleaved during processing of the protein. Therefore, the muteins of the invention often comprise pure IL-6 muteins, pure -1aa IL-6 muteins, pure -2aa IL-6 muteins, or a mixture of two or three of IL-6, -1aa IL-6 and -2aa IL-6 muteins.

The present invention also includes equivalent variants of the muteins described above and the nucleic acid molecules that encode such variants. Equivalent variants include proteins comprising additions, deletions and substitutions in the amino acid and nucleotide sequences of the muteins of the invention and the corresponding nucleic acid molecules. Variants are included in the invention as long as the resulting muteins and nucleic acid molecules continue to satisfy the structural and functional criteria described above, i.e., retain enhanced biological activity. An amino acid or nucleotide sequence that is substantially the same as another sequence, but that differs from the other sequence by means of one or more substitutions, additions or deletions is considered to be an equivalent sequence. Preferably, less than 25%, more preferably less than 10%, and most preferably less than 5% of the total number of amino acids or nucleotides in the muteins of the invention are substituted for or added to in the equivalent sequences. The substitutions include those at positions corresponding to positions 171 and 175 of mature, native IL-6, as long as the resulting mutein retains significant biological activity.

For example, it is known to substitute amino acids in a sequence with equivalent amino acids. Groups of amino acids considered normally to be equivalent are:

(a) Ala(A) Ser(S) Thr(T) Pro(P) Gly(G);
(b) Asn(N) Asp(D) Glu(E) Gln(Q);
(c) His (H) Arg(R) Lys(K);
(d) Met(M) Leu(L) Ile(I) Val(V); and
(e) Phe(F) Tyr(Y) Trp(W).

Additions to the full-length and truncated IL-6 muteins may be made internally or at the C-terminal or N-terminal ends by adding the corresponding nucleic acid sequences at the appropriate location of the nucleic acid molecules encoding an IL-6 mutein, and expressing the nucleic acid molecules. Examples of internal additions to the nucleic acid molecules include the introns present in genomic DNA. The introns are not expressed in a suitable eukaryotic host cell.

The present invention also includes nucleic acid molecules that encode any of the muteins of the invention described above. The nucleic acid molecules are preferably recombinant nucleic acid molecules, and may be DNA or RNA. The term "recombinant nucleic acid molecule" in this specification is understood to mean a molecule having a nucleic acid sequence that has been intentionally manipulated into a form that does not occur naturally.

Equivalents of the nucleic acid molecules encoding IL-6 muteins also include silent mutations at sites that do not alter the amino acid sequence expressed. Preferably, the silent mutation results in increased expression in a particular host.

UTILITY

The IL-6 muteins of the invention are useful in the in vitro and in vivo proliferation and differentiation of B cells, T cells, megakaryocytes, and multi-potential hematopoietic progenitor cells. In addition, the IL-6 muteins induce various acute phase proteins in liver cells. The stimulation of proliferation of megakaryocytes leads to the production of platelets. As a result of these biological activities, the IL-6 muteins are useful in immunotherapeutic and anti-inflammation compositions. The muteins may also be used for the treatment of patients suffering from thrombocytopenia and patients undergoing chemotherapy or bone marrow transfers.

Preferably, the IL-6 muteins of the present invention are used at lower dosages than native IL-6, since the lower dosages achieve the same level of biological activity.

Preparation of the Muteins

The muteins of the present invention may be prepared by methods known in the art. Such methods include synthesizing the IL-6 muteins chemically from individual amino acids, mutating or synthesizing DNA encoding the IL-6 mutein and using the DNA to produce recombinant protein.

Chemical Synthesis of the Muteins

The muteins of the present invention and DNA encoding the muteins may also be chemically synthesized by methods known in the art. Suitable methods for synthesizing the muteins are described by Stuart and Young in "Solid Phase Peptide Synthesis," Second Edition, Pierce Chemical Company (1984). Suitable methods for synthesizing DNA are described by Caruthers in Science 230, 281–285 (1985).

Recombinant Protein

The muteins may be prepared by providing DNA that encodes the muteins; amplifying the DNA or cloning the DNA in a suitable host; expressing the DNA in a suitable host; and harvesting the muteins.

Providing DNA

Chemical Synthesis from Nucleotides

The DNA may be synthesized chemically from the four nucleotides in whole or in part by methods known in the art. Such methods include those described by Caruthers in Science 230, 281–285 (1985).

DNA may also be synthesized by preparing overlapping double-stranded oligonucleotides, filling in the gaps, and ligating the ends together. The DNA may be cloned in a suitable host cell and expressed. The DNA and mutein may be recovered from the host cell. See, generally, Sambrook et al, "Molecular Cloning," Second Edition, Cold Spring Harbor Laboratory Press (1987).

Mutants by site-Directed Mutagenesis

Mutant DNA expressing the mutated proteins may be prepared from wild-type IL-6 DNA by site-directed mutagenesis; see, for example, Zoller and Smith, *Nucl. Acids Res.* 10, 6487–6500 (1982); *Methods in Enzymology* 100, 468–500 (1983); and *DNA* 3, 479–488 (1984). Wild-type IL-6 DNA may be obtained by the method described by Jambou, R. C. et al., *Proc. Natl. Acad. Sci., USA* 85 9426–9430 (1988). Alternatively, wild-type IL-6 DNA may be commercially obtained from Beckman Instruments Incorporated, 2500 N. Harbor Blvd., Fullerton, Calif. 92634, catalog number 267406. The substitution of cysteine residues may be accomplished by methods described in U.S. Ser. No. 07/724,698 and the corresponding PCT application.

Amplifying DNA

The mutant DNA obtained may be amplified by methods known in the art. One suitable method is the polymerase chain reaction (PCR) method described by Saiki et al. in *Science* 239, 487 (1988), Mullis et al in U.S. Pat. No. 4,683,195 and by Sambrook, Fritsch and Maniatis (eds) in *Molecular Cloning, A Laboratory Manual*, Second Edition, Cold Spring Harbor Laboratory Press (1989). It is convenient to amplify the clones in the lambda-gt10 or lambda-gt11 vectors using lambda-gt10 or lambda-gt11-specific oligomers as the amplimers (available from Clontech, Palo Alto, Calif.).

Expressing DNA

The DNA encoding the mutein of the invention may be replicated and used to express recombinant protein following insertion into a wide variety of host cells in a wide variety of cloning and expression vectors. The host is preferably unicellular, and may be prokaryotic or eukaryotic.

Cloning vectors may comprise segments of chromosomal, non-chromosomal and synthetic DNA sequences. Some suitable prokaryotic cloning vectors include plasmids from *E. coli*, such as colE1, pCR1, pBR322, pMB9, pUC, pKSM, and RP4. Prokaryotic vectors also include derivatives of phage DNA such as M13 fd, and other filamentous o single-stranded DNA phages.

Vectors for expressing muteins in bacteria, especially *E. coli*, are also known. Such vectors include the pK233 (or any of the tac family of plasmids), T7, and lambda $P_L$. Examples of vectors that express fusion muteins are PATH vectors described by Dieckmann and Tzagoloff in *J. Biol. Chem.* 260, 1513–1520 (1985). These vectors contain DNA sequences that encode anthranilate synthetase (TrpE) followed by a polylinker at the carboxy terminus. For example, PATH 23 is an ampicillin-resistance plasmid containing a gene that encodes the amino-terminal 337 amino acids of trpE (anthranilate synthase component I) adjacent to, and it reading frame at its 3' end with, a polylinker containing a HindIII site. A general description of the trpE operon may be found in Miller and Reznikoff, eds., *The Operon*, Cold Spring Harbor Laboratory, pp. 263–302 (1978). Other sources of DNA that encode all or part of trpE and lacZ are readily available. Such other sources may be found, for example, in Pouwels, et al., *Cloning Vectors, A Laboratory Manual*, Elsevier, 1985. Suitable trpE sequences may be isolated from plasmids having the following identifying codes in the Pouwels, et al. manual; I-A-ii-3 (pDF41 and 42), I-A-iv-23 (pRK352), I-B-ii-4 (pMBL24), I-B-ii-1 (ptrpED-5-1), I-D-i-3 (pEP70-pEP75), and I-D-i-4 (pEP165 and pEP168). Other expression vector systems are based on beta-galactosidase (pEX); maltose binding protein (pMAL); glutathione S-transferase (pGST) - see *Gene* 67, 31 (1988) and Peptide Research 3, 167 (1990).

Vectors useful for cloning and expression in yeast are available. A suitable example is the $2\mu$ circle plasmid.

Suitable cloning/expression vectors for use in mammalian cells are also known. Such vectors include well-known derivatives of SV40, adenovirus, cytomegalovirus (CMV) retrovirus-derived DNA sequences and vectors derived from combination of plasmids and phage DNA.

Further eukaryotic expression vectors are known in the art (e.g., P. J. Southern and P. Berg, *J. Mol. Appl. Genet.* 1, 327–341 (1982); S. Subramani et al, *Mol. Cell. Biol.* 1, 854–864 (1981); R. J. Kaufmann and P. A. Sharp, "Amplification And Expression Of Sequences Cotransfected with A Modular Dihydrofolate Reductase Complementary DNA Gene," *J. Mol. Biol.* 159, 601–621 (1982); R. J. Kaufmann and P. A. Sharp, *Mol. Cell. Biol.* 159, 601–664 (1982); S. I. Scahill et al, "Expression And Characterization Of The Product Of A Human Immune Interferon DNA Gene In Chinese Hamster Ovary Cells," *Proc. Natl. Acad. Sci., USA* 80, 4654–4659 (1983); G. Urlaub and L. A. Chasin, *Proc. Natl. Acad. Sci., USA* 77, 4216–4220, (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Useful expression hosts include well-known prokaryotic and eukaryotic cells. Some suitable prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRC1, Pseudomonas, Bacillus, such as *Bacillus subtilis*, and Streptomyces. Suitable eukaryotic cells include yeasts and other fungi, insect, animal cells, such as COS cells and CHO cells, human cells and plant cells in tissue culture.

Overexpressing DNA

The mutein of the invention may be overexpressed behind an inducible promoter and purified by affinity chromatography using specific IL-6 antibodies. As another alternative, the overexpressed protein may be purified using a combination of ion-exchange, size-exclusion, and hydrophobic interaction chromatography using methods known in the art. These and other suitable methods are described by Marston, "The Purification of Eukaryotic Polypeptides Expressed in *E. coli*" in *DNA Cloning*, D. M. Glover, Ed., Volume III, IRL Press Ltd., England, 1987.

Fusion Proteins

The muteins of the invention may be expressed in the form of a fusion protein with an appropriate fusion partner. The fusion partner preferably facilitates purification and identification. Increased yields may be achieved when the fusion partner is expressed naturally in the host cell. Some useful fusion partners include beta-galactosidase (Gray, et al., *Proc. Natl. Acad. Sci., USA* 79, 6598 (1982)); trpE (Itakura et al., *Science* 198, 1056 (1977)); protein A (Uhlen et al., *Gene* 23 369 (1983)); glutathione S-transferase (Johnson, *Nature* 338, 585 (1989)); Van Etten et al., *Cell* 58, 669 (1989)); and maltose binding protein (Guan et al., *Gene* 67, 21–30 (1987); Maina et al., *Gene* 74, 36–373 (1988); Riggs, P., in Ausebel, F. M. et al (eds) Current Protocols in Molecular Biology, Greene Associates/Wiley Interscience, New York (1990)).

Such fusion proteins may be purified by affinity chromatography using reagents that bind to the fusion partner. The reagent may be a specific ligand of the fusion partner or an antibody, preferably a monoclonal antibody. For example, fusion proteins containing betagalactosidase may be purified by affinity chromatography using an anti-beta-galactosidase antibody column (Ullman, *Gene*. 29, 27–31 (1984)). Similarly, fusion proteins containing maltose binding protein may be purified by affinity chromatography using a column containing cross-linked amylose; see Guan, European Patent Application 286,239.

Preferably, the DNA that encodes the fusion protein is engineered so that the fusion protein contains a clearable site between the mutein and the fusion partner. More preferably, the fusion protein is linked to the carboxy-terminal side of the mutein of the invention, though linkage at the amino-terminal side is also possible.

Both chemical and enzymatic cleavable sites are known in the art. Suitable examples of sites that are cleavable enzymatically include sites that are specifically recognized and cleaved by collagenase (Keil et al., *FEBS Letters* 56, 292–296 (1975)); enterokinase (Hopp et al., *Biotechnology* 6, 1204–1210 (1988)); factor Xa (Nagai et al., *Methods Enzymol.* 153, 461–481 (1987)); and thrombin (Eaton et al., *Biochemistry* 25, 505 (1986)). Collagenase cleaves between proline and X in the sequence Pro-X-Gly-Pro wherein X is a neutral amino acid. Enterokinase cleaves after lysine in the sequence Asp-Asp-Asp-Asp-Lys. Factor Xa cleaves after arginine in the sequence Ile-Glu-Gly-Arg. Thrombin cleaves between arginine and glycine in the sequence Arg-Gly-Ser-Pro.

Specific chemical cleavage agents are also known. For example, cyanogen bromide cleaves at methionine residues in proteins.

In one embodiment, the IL-6 muteins of the present invention are made by modifying the wild-type IL-6 nucleic acid sequence so that it contains the codons that represent the desired amino acid substitution. The resulting DNA is then expressed in a prokaryotic or eukaryotic system, purified, analysed for biological activity and administered therapeutically.

Initially, a high level IL-6-$\beta$-galactosidase expression vector, p340, described by Jambou et al., *Proc. Natl. Acad. Sci., USA* 85 9426–9430 (1988), is modified to contain a synthetic minicistron that further increases the levels of protein expression. (See Jambou et al., *Proc. Natl. Acad. Sci., USA* 139 4116–4121 (1988)) The modified vector is denoted p478. (See Snouwaert, J. N., et al., *J. Immunol.* 146, 585–591 (1991)) The p478 vector is used for the production of wild-type IL-6 as a control and for alteration to produce the IL-6 muteins of the present invention. The p478 vector allows the production of large quantities of IL-6 and IL-6 muteins in 10 ml cultures.

In order to select for mutated IL-6 in subsequent cloning procedures more efficiently, a phenotypic change is introduced into the p478 expression vector. See FIG. 5. The p478 vector is altered so that the $\beta$-galactosidase gene is out of frame with the initiating methionine of IL-6. This is done by replacing the nucleic acid segment that encodes C-terminal amino acids of IL-6 with a 29 bp fragment that encodes three termination codons and KpnIII and HindIII restriction sites. The replaced IL-6 nucleic acid segment is located between the BglII and PmlI restriction sites of the vector. As a result, functional $\beta$-galactosidase is not produced by the expression system. When the expression system is exposed to a colorimetric $\beta$-galactosidase substrate, the reaction product is not formed. The absence of the colored reaction product imbues the vector with a white phenotype. The vector is denoted p560. Expression systems containing the p560 vector are selected based on the white phenotype.

Once an expression system that contains the p560 vector has been selected, complementary oligonucleotides containing mutated C-terminal IL-6 sequences are cloned into the vector. The mutated oligonucleotides serve to introduce amino acid substitutions into IL-6 corresponding to positions 171 and 175 of the wild-type.

In order to produce a p560 expression vector with mutated IL-6 sequences, the 29 bp segment, originally inserted between the BglII and PmlI restriction sites of the vector, is removed and replaced with oligonucleotides that contain sequences that encode the IL-6 C-terminal amino acid substitution(s) of the present invention. During the procedure, the β-galactosidase gene is placed back in frame with the initiating methionine of the IL-6 mutein. Vectors that have properly incorporated the oligonucleotides will produce a functional β-galactosidase enzyme. The colorimetric reaction product produced by the functional β-galactosidase enzyme is used to distinguish transformed vectors containing IL-6 muteins from non-transformed vectors.

After ligation of the particular oligonucleotides into the p560 expression vector, the system is induced to express the mutated IL-6-β-galactosidase fusion protein. The expression system is exposed to a colorimetric substrate, such as 5-Bromo-4-chloro-3-indolyl β-d-galactopyranoside (BCIG), that is acted upon by the β-galactosidase enzyme, producing a colored reaction product. The colored colonies are selected and screened for the correct oligonucleotide insert using the polymerase chain reaction (PCR). Selected vectors are further analyzed by dideoxy sequencing.

Following expression of the desired mutated IL-6-β-galactosidase fusion protein, the mutated IL-6 portion is enzymatically cleaved to release the IL-6 mutein of the present invention. Lastly, the IL-6 mutein is purified by standard techniques and assayed for biological activity and binding capacity.

Purifying Proteins

The muteins of the present invention are purified by methods known in the art. Such methods include affinity chromatography using specific antibodies. Alternatively, the muteins may be purified using a combination of ion-exchange, size-exclusion, hydrophobic interaction chromatography and gel filtration using methods known in the art. These and other suitable methods are described by Marston, "The Purification of Eukaryotic Proteins Expressed in *E. coli*" in *DNA Cloning*, D. M. Glover, Ed., Volume III, IRL Press Ltd., England, 1987 and by Sofer et al. in *Biotechniques*, 198–203 (1983).

The muteins of the present invention are preferably essentially pure. For the purposes of this specification, essentially pure means that the muteins are free from all but trace amounts of other proteins as well as of materials used during the purification process. Materials used in the purification process include detergents, affinity binding agents and separation films. Detergents include sodium dodecyl sulfate and sarcosine. Affinity binding agents include agarose, avidin-agarose, streptavidin-agarose, biotin and biotinylated proteins. Separation films include nitrocellulose paper and nitrocellulose/-cellulose acetate paper.

A mutein is considered to be essentially pure if it is at least 85%, preferably at least 95%, and more preferably at least 98% free of such materials.

EXAMPLES

Example 1

Mutagenesis

As described in the "Fusion Proteins" Section, supra, and as depicted in FIG. 5, a phenotypic change is introduced into the wild-type IL-6 expression vector p478 in order to select for IL-6 muteins later in the mutein construction process. The p478 vector is altered by replacing the BglII-PmlI segment of the vector with a 29 bp oligonucleotide. The sequences of the 29 bp oligonucleotide (a) and its complement (b) are as follows:

a=5′ GAT CTT AAG TAG TAG GTA CCA AGC TTG AC b=3′ AA TTC ATC ATC CAT GGT TCG AAG TG (See SEQ. ID. NOS. 9–10)

These oligonucleotides are made on a DNA synthesizer (Applied Biosystems 380A, Foster City, Calif.) and purified by reverse-phase high-performance liquid chromatography. Reagents are obtained from American Bionetics (Hayward, Calif.). The altered p478 vector is denoted p560.

In order to introduce mutated C-terminal IL-6 nucleic acid sequences into the p560 expression vector, a 129 bp nucleic acid fragment that contains the mutated sequences is produced and cloned into the p560 vector. The fragment is constructed by joining two complementary oligonucleotide pairs, c-f and d-e. The oligonucleotide pair c-f is synthesized to have one or more point mutations in the sequence encoding the C-terminus of IL-6. A point mutation is made by the saturation mutagenesis method described by Hutchinson et al., *Proc. Natl. Acad. Sci., USA* 83 710–714 (1986). Using the method, oligonucleotides c and f are mutagenized by using a mixture of phosphoramidites in the synthesis mixes during their synthesis. The synthesis mixture contains 96% of the four deoxynucleotides thymidine, adenine, guanine and cytosine and a 4% equimolar mixture of the four comparable phosphoramidites. By contaminating one phosphoramidite with a small amount of each of the other three phosphoramidites during synthesis of the oligonucleotide, an oligonucleotide is obtained that has one or more mutations in its sequence compared to the wild-type sequence.

The other oligonucleotide pair, d-e, is sythesized and purified by the following procedure.

I. Automated Synthesis Procedures

The 2-cyanoethyl phosphoramidites are purchased from Applied Biosystems Inc. The procedure includes condensation of nucleoside phosphoramidites to 30 mg of a nucleoside-derivatized controlled pore glass (CPG) bead support (500 Angstrom pore diameter), using DNA synthesizer from Applied Biosystems Inc., Type 380B-02. The cycles includes detritylation with 2% trichloroacetic acid in dichloromethane; condensation using tetrazol as an activating proton donor; capping with acetic anhydride and dimethylaminopyridine; detritylation using 2% trichloroacetic acid in dichloromethane; and oxidation of the phosphite to the phosphate with 0.1M $I_2/H_2O$/lutidine/tetrahydrofuran. Cycle time is approximately 30 minutes. Yields at each step are essentially quantitative and are determined by collection and spectroscopic examination of the dimethoxytrityl alcohol released during detritylation.

II. Oligodeoxyribonucleotide Deprotection and Purification Procedures

The solid support is removed from the column and exposed to 1 ml concentrated ammonium hydroxide at 60° C. for 16 hours in a closed tube. Ammonia is removed and the residue is applied to a preparative 12% polyacrylamide gel using a Tris-borate buffer (pH 8) containing 7M urea. Electrophoresis is carried out at 20 volts/cm for 5 hours after which the band containing the product is identified by UV shadowing of a fluorescent plate. The band is excised and eluted with 1 ml double distilled water overnight at room temperature. This solution is filtered and the supernatant is extracted (3×300 microliter) with n-butanol. The water phase is placed on a Sephadex G50 column (Pharmacia) (1×10 cm). The elution is monitored by UV absorbance at 260 nm and the appropriate fraction collected, quantitated by UV absorbance in a fixed volume and evaporated to dryness at room temperature in a vacuum centrifuge.

III. 5'- Phosphorylation of d and e Sequences

In order to phosphorylate 5'-ends of the d and e new-phosphorylating reagent as described by T. Horn et al., Tetrahedron Letters 27: 4705–08 (1986) is used. Only the ends of the nucleotides that are to be joined together will be phosphorylated.

The synthesis of d and e is described as in I. Automated Synthesis Procedure, but after the last cycle, the phosphorylating reagent

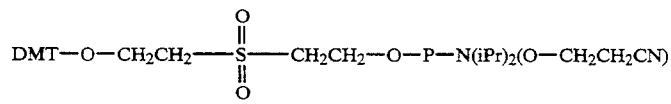

(Glen Corp. Inc.) (DMT is dimethoxytrityl group; iPr is isopropyl) is condensed to each of the sequences d and e using tetrazol as an activating proton donor, followed by capping with acetic anhydride and dimethylaminopyridine; detritylation using 2% trichloroacetic acid in dichloromethane; and oxidation of the phosphite to the phosphate with 0.1M I$_2$/H$_2$O/lutidine/tetrahydrofuran. Cycle time is approximately 30 minutes.

The 5'-phosphorylated d and e are purified and quantitated by the procedure described in II above.

The complete sequence of the four oligonucleotides is as follows:

c = 5' GAT CTT TTA AGG AGT TCC TGC AGT CTA GCC TGA GAG CTC TTC GGC AAA TGT CAG ACT CTG TGC C d = 5' TGT TGG TCC TGT TGG TCC TGC TGG TGC TTT TGG CCC AAG AGG TCT CGC TGG CCC ACA AGG TCC AC e = 5' GTG GAC CTT GTG GGC CAG CGA GAC CTC TTG GGC CAA AAG CAC CAG CAG GAC CAA CAG GAC C f = 5' AAC AGG CAC AGA ATC TGA CAT TTG CCG AAG AGC TCT CAG GCT AGA CTG CAG GAA CTC CTT AAA A (See SEQ. ID. NOS. 11-14)

The non-underlined part of oligonucleotides c and f as well as the complete oligonucleotides d and e are identical to the original segments in the wild-type IL-6 expression vector (p478). The underlined parts of the oligonucleotides represent the codons that, when mutated, encode a substituted C-terminal amino acid of an IL-6 mutein of the present invention. In particular, the TTT codon of oligonucleotide c codes for Phenylalanine at position 171 of the wild-type IL-6. When the TTT codon is mutated to TTG, TTA, CTT, CTC, CTA or CTG, Phenylalanine$^{171}$ is substituted with Leucine. Similarly, codon CTG of oligonucleotide c codes for Leucine at position 175 of wild-type IL-6. When codon CTG is mutated to ATG, Leucine$^{175}$ is substituted with Methionine.

Following synthesis, the oligonucleotides are purified by HPLC. Once purified, complementary oligonucleotides c-f and d-e are annealed and kinased. The annealed pairs are then ligated to form a single 129 bp fragment with oligonucleotides c and d functioning as the coding strand. The complete sequence of the 129 bp fragment is as follows:

```
                c
5' GAT CTT TTA AGG AGT TCC TGC AGT CTA GCC TGA GAG CTC TTC GGC
3'     AA AAT TCC TCA AGG ACG TCA GAT CGG ACT CTC GAG AAG CCG d
AAA TGT CAG ACT CTG TGC CTG TTG GTC CTG TTG GTC CTG CTG GTG CTT
TTT ACA GTC TGA GAC ACG GAC AAC CAG GAC AAC CAG GAC GAC CAC GGA f
TTG GCC CAA GAG GTC TCG CTG GCC CAC AAG CTG CAC 3'              129
AAC CGG GTT CTC CAG AGC GAC CGG GTG TTC GAC GTC 5'
                                                  e
```

(See SEQ. ID. NOS. 15-16)

The 129 bp fragment contains the last 46 bases of the IL-6 sequence and part of the collagen linker of the fusion protein. The size of the fragment is confirmed by agarose gel electrophoresis and purified by electroelution.

Following excision of the 29 bp fragment that replaced the BglII-PmlI segment of the p478 vector, the 129 bp fragment is cloned into the p560 vector at the BglII cleavage site. (See FIG. 5) This reconstruction of the vector results in an expression vector with the complete IL-6-β-galactosidase fusion protein with a point mutation in the C-terminal region of IL-6 that encodes an amino acid substitution of the present invention.

Once p560 vectors containing mutated IL-6 C-terminal sequences are constructed, XL-1 Blue cells (Stratagene, La Jolla, Calif.) are transformed with the vector according to standard procedures. Part of the transformation mixture is plated out on Luria-broth culture plates that are coated with ampicillin and tetracycline as selection markers; isopropyl-B-D-thiogalactopyranoside (IPTG) for induction of fusion protein synthesis; and 5-Bromo-4-chloro-3-indolyl β-d-galactopyranoside (BCIG) as a substrate for β-galactosidase to permit selection of colonies by their dark-blue color.

Part of the transformation mixture is incubated in L-broth-ampicillin/tetracycline as an overnight culture. This first transformation results in mixed colonies because the complementary oligonucleotides c and f are likely to have different sequences due to the mutagenesis procedure.

The colonies are washed off of the plates with 2 ml of SOB medium. The recipe for SOB medium is as follows:
1) Bacto tryptone (2%)
2) Bacto yeast extract (0.5%)
3) NaCl (10 mM)
4) KCl (2.5 mM)
5) $MgCl_2$ (10 mM)
6) $MgSO_4$ p560 DNA is purified and used for a consecutive transformation of XL-1 Blue cells to obtain pure colonies. This retransformation is done after the DNA is digested with HindIII. The HindIII digestion results in a reduced background, because it only cleaves plasmid p560 without the 129 bp insert.

The transformation mixture is plated out on L-broth-ampicillin/tetracycline plates coated with IPTG and BCIG. A total of 250 blue colonies are checked for having the 129 bp insert by the polymerase chain reaction (PCR). Two oligonucleotides are used. One inside the IL-6 gene and one in the expression vector (collagen linker). PCR is carried out according to standard procedures. (Saiki et al. in *Science* 239, 487 (1988), Mullis et al in U.S. Pat. No. 4,683,195 and by Sambrook, Fritsch and Maniatis (eds) in *Molecular Cloning, A Laboratory Manual*, Second Edition, Cold Spring Harbor Laboratory Press (1989)) The plasmids that have the correct size insert are further analyzed by dideoxy sequencing.

Example 2

Expression, purification and quantitation of recombinant IL-6 muteins

Detailed description of the bacterial expression system used in the invention has previously been published. Snouwaert, J. N., et al., *J. Immunol.* 146, 585–591 (1991); Jambou, R. C., et al., *Proc. Natl. Acad. Sci., U.S.A.* 139, 4116–4121 (1988); Snouwaert, J. N., et al., *J. Biol. Chem.* 266, 23097–23102 (1991).

The expression vector containing the DNA for the fusion protein with the desired IL-6 mutein is transformed into *Escherichia coli* JM101. Single ampicillin resistant colonies are picked to inoculate 10 ml broth cultures. At log phase growth of the bacteria, expression of the fusion protein is induced by addition of 100 μl of isopropyl-B-D-thiogalactopyranoside (IPTG) (25 mg/ml) β-galactosidase activity is measured and at maximum levels of activity, bacteria are pelleted by centrifugation and stored at −20° C. until further use.

Bacteria are resuspended in 1 ml 0.5X phosphate buffered saline (PBS) and lysed by repeated freezing and thawing after lysozyme treatment. To reduce viscosity, the lysate is sonicated and the fusion protein pelleted by centrifugation. The pellet is washed to remove soluble contaminants and the fusion protein is solubilized in 2% sodium lauroyl safcosine. Insoluble contaminants are removed by centrifugation and the fusion protein is precipitated by two rounds of selective ammonium sulfate precipitation. The IL-6 mutein is cleaved from the β-galactosidase by collagenase treatment prior to quantitation or use in bioassays.

Because of the high amounts of IL-6 mutein expressed in the induced bacteria, it is possible to quantitate the protein preparations by denaturing sodium dodecyl sulfate-polyacrylamide gel electrophoresis under reducing conditions followed by Coomassie staining and scanning laser densitometry.

Example 3

Bioassay of IL-6 Muteins

The hepatocyte stimulation assay using human hepatoma cell line HEP3B2 is carried out in duplicate serial dilutions of three or more independent preparations of each IL-6 mutein. The biological activity is determined from dose response curves prepared for each protein preparation. To minimize variation, a duplicate protein preparation of wild-type IL-6 is used in each 96-well tissue culture plate to calculate the activity of two (HEP3B2) IL-6 muteins on the same plate as a percentage of wild-type IL-6 activity. (See FIG. 6)

Cells from the human hepatoma cell line HEP3B2 are maintained in DMEM-H medium supplemented with 10% fetal bovine serum and penicillin/streptomycin. On the day before treatment, cells are trypsinized and plated on 96-well tissue culture plates at a density sufficient to give confluent monolayers after overnight growth. The next day, the IL-6 muteins to be tested are diluted in maintenance medium supplemented with $10^{-6}$ dexamethasone. Each dilution is tested in duplicate by adding 100 μl/well to the plated cells. Conditioned medium is collected after 48 hours and assayed for fibrinogen production by a sandwich ELISA using a commercially available capture antibody (IgG fraction, goat anti-human fibrinogen; Cappel, Durham, N.C.) and a peroxidase-conjugated detection antibody (peroxidase conjugated IgG fraction, goat anti-human fibrinogen; Cappel, Durham, N.C.). Color is developed using a peroxidase substrate (Kirkegaard & Perry, Gaithersburg, Md.). The OD405 is determined on a $V_{max}$ ELISA plate reader (Molecular Devices Corp., Palo Alto, Calif.).

The activity of native IL-6 and IL-6 muteins in the assay is defined as the IL-6 concentration that causes a doubling of fibrinogen secretion. The activity of each IL-6 mutant is calculated by taking the mean and the standard error of the mean of the activities determined for the independent protein preparations. The results are shown in FIG. 6.

Example 4

Binding assay of IL-6 Muteins

Binding competition assays are performed using human recombinant IL-6 derived from *Escherichia coli* (Genetics Institute, Cambridge, Mass.). IL-6 is radioiodinated using the Bolton-Hunter reagent (New England Nuclear, Wilmington, Del.) as described by Faltynek, C. R., et al., *J. Immunol.* 136, 4134–4139 (1986). The specific activity of the radiolabelled IL-6 is 22 μC/μg. For the binding experiments, a human myeloma cell line U-266 is used. The cells are grown in RPMI 1640 medium supplemented with 10% fetal bovine serum, 2 mM L-glutamine and penicillin/streptomycin. This medium is also used for making the dilutions of the IL-6 muteins and as the binding medium. The fetal bovine serum batches are routinely tested for IL-6 activity and only batches that show negligible IL-6 activity are used for competition binding assays.

Cells are harvested by low speed centrifugation, washed once in Ca++/Mg+ free phosphate buffered saline and resuspended at a concentration of $10^7$ cells/ml medium at 4° C. The IL-6 muteins are treated with collagenase and diluted immediately afterwards to the desired concentrations in binding medium. $^{125}$I-IL-6 is diluted to a concentration of 16 ng/ml. Thereafter, 100 μl of cells, 50 μl of IL-6 mutein and 50 μl of $^{125}$I-IL-6 are transferred in rapid succession using a 12-well multichannel pipet into round-bottom, polyvinyl 96-well plates (Dynatech, Chantilly, Va.) to yield a final concentration of $10^6$ cells/200 μl, 0.2 nM labelled IL-6 and varying concentrations of IL-6 mutein (1600 to 0.194 ng/200 μl).

Binding is performed by sealing the plates with acetate plate sealers (ICN Biomedicals, Costa Mesa, Calif.) and end-over rotation for 3 hours at 4° C. Thereafter, cells are quickly pelleted by spinning the plates in a Beckman TJ-6 table-top centrifuge (Beckman Instruments, Fullerton, Calif.). The supernatants are aspirated using a 12 channel aspiration/washing device (Immuno Wash 12, Nunc, Denmark). The cell pellets are washed once with 200 μl of ice-cold Ca++/Mg+ free Hank's balanced salt solution (HBSS), resuspended in 200 μl of HBSS, transferred to scintillation vials and counted in a gamma counter.

Scatchard analysis and the competition binding experiments is performed by measuring the binding in the presence of a constant concentration of $^{125}$I-IL-6 and varying concentrations of unlabelled IL-6 mutein. The results of the Scatchard and competition binding assays are analyzed using a non-linear curve fitting program LIGAND. (Analytical Biostatistical Section, Division of Computer Research and Technology, National Institutes of Health, Bethesda, Md. 20892) After the $K_d$ of wild-type IL-6 and the IL-6 mutein for the receptor are calculated, the receptor binding capacity of the IL-6 muteins are expressed as a percentage of receptor binding of wild-type IL-6. The percentage is calculated by dividing the $K_d$-wild-type IL-6 by the $K_d$-IL-6 mutein. An apparent $IC_{50}$ is calculated using the EBDA/LIGAND program. (See FIG. 6)

What is claimed is:

1. A mutein of human IL-6 having increased activity wherein the Phenylalanine residue at position 171 of the native IL-6 sequence shown in SEQ. ID. NOS. 1-2 and in FIG. 1 is replaced by a Leucine residue and/or the Leucine residue at position 175 of the native IL-6 sequence shown in SEQ. ID. NOS. 1-2 and in FIG. 1 is replaced by a Methionine residue.

2. The mutein of claim 1 wherein the Phenylalanine residue at position 171 of the native IL-6 sequence shown in SEQ. ID. NOS. 1-2 and in FIG. 1 is replaced by a Leucine residue.

3. The mutein of claim 1 wherein the Leucine residue at position 175 of the native IL-6 sequence shown in SEQ. ID. NOS. 1-2 and in FIG. 1 is replaced by a Methionine residue.

4. The mutein of claim 1 wherein the Phenylalanine residue at position 171 of the native IL-6 sequence shown in SEQ. ID. NOS. 1-2 and in FIG. 1 is replaced by a Leucine residue and the Leucine residue at position 175 of the native IL-6 sequence shown in SEQ. ID. NOS. 1-2 and in FIG. 1 is replaced by a Methionine residue.

5. The mutein of claim 1 wherein the mutein has up to 28 amino acids deleted from the amino terminal end of the mutein.

6. The mutein of claim 1 wherein the mutein has up to 22 amino acids deleted from the amino terminal end of the mutein.

7. The mutein of claim 1 wherein the mutein has 22 amino acids deleted from the amino terminal end of the mutein.

8. The mutein of claim 1 wherein the mutein has at least 25 percent greater IL-6 mediated biological activity than that of IL-6 having the wild-type sequence.

9. The mutein of claim 1 wherein the mutein has at least 50 percent greater IL-6 mediated biological activity than that of IL-6 having the wild-type sequence.

10. The mutein of claim 2 wherein the mutein has greater binding capacity for an IL-6 receptor as compared with that of IL-6 having the wild-type sequence.

11. The mutein of claim 3 wherein the mutein has less binding capacity for an IL-6 receptor as compared with that of IL-6 having the wild-type sequence.

12. The mutein of claim 1 wherein the cysteine residues at positions 45 and 51 of the native IL-6 sequence shown in SEQ. ID. NOS. 1-2 and in FIG. 1 are replaced by another amino acid residue.

13. The mutein of claim 12 wherein the amino acid residue is a neutral amino acid residue.

14. The mutein of claim 12 wherein the amino acid residue is serine.

15. The mutein of claim 12 wherein the amino acid residue is alanine.

* * * * *

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 564 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..558

( i x ) FEATURE:
        ( A ) NAME/KEY: matpeptide
        ( B ) LOCATION: 1..555

( x i ) SEQUENCE DESCRIPTION: SEQ ID NO:1:

```
GCT  CCG  GTT  CCG  CCA  GGA  GAA  GAT  TCC  AAA  GAT  GTA  GCC  GCC  CCA  CAC   048
Ala  Pro  Val  Pro  Pro  Gly  Glu  Asp  Ser  Lys  Asp  Val  Ala  Ala  Pro  His
 1              5                        10                       15

AGA  CAG  CCG  CTC  ACC  TCT  TCA  GAA  CGA  ATC  GAT  AAA  CAA  ATT  CGG  TAC   096
Arg  Gln  Pro  Leu  Thr  Ser  Ser  Glu  Arg  Ile  Asp  Lys  Gln  Ile  Arg  Tyr
              20                        25                       30

ATC  CTC  GAC  GGG  ATA  TCA  GCG  CTG  AGA  AAA  GAG  ACC  TGT  AAC  AAG  AGT   144
Ile  Leu  Asp  Gly  Ile  Ser  Ala  Leu  Arg  Lys  Glu  Thr  Cys  Asn  Lys  Ser
         35                        40                       45

AAC  ATG  TGT  GAA  AGC  AGT  AAA  GAA  GCA  CTG  GCA  GAA  AAC  AAC  CTG  AAC   192
Asn  Met  Cys  Glu  Ser  Ser  Lys  Glu  Ala  Leu  Ala  Glu  Asn  Asn  Leu  Asn
    50                        55                       60

CTT  CCG  AAG  ATG  GCT  GAA  AAA  GAT  GGA  TGT  TTT  CAA  TCT  GGA  TTC  AAT   240
Leu  Pro  Lys  Met  Ala  Glu  Lys  Asp  Gly  Cys  Phe  Gln  Ser  Gly  Phe  Asn
 65                       70                       75                       80

GAG  GAA  ACT  TGT  CTG  GTG  AAA  ATC  ATC  ACA  GGC  CTT  TTG  GAA  TTT  GAG   288
Glu  Glu  Thr  Cys  Leu  Val  Lys  Ile  Ile  Thr  Gly  Leu  Leu  Glu  Phe  Glu
                   85                       90                       95
```

```
GTA TAC CTA GAG TAC CTC CAG AAC AGA TTT GAG AGT AGT GAG GAA CAA   336
Val Tyr Leu Glu Tyr Leu Gln Asn Arg Phe Glu Ser Ser Glu Glu Gln
            100             105             110

GCG AGA GCT GTC CAG ATG TCG ACC AAA GTC CTG ATC CAG TTT CTG CAG   384
Ala Arg Ala Val Gln Met Ser Thr Lys Val Leu Ile Gln Phe Leu Gln
        115             120             125

AAA AAG GCA AAA AAT CTA GAT GCA ATA ACC ACC CCG GAT CCA ACC ACA   432
Lys Lys Ala Lys Asn Leu Asp Ala Ile Thr Thr Pro Asp Pro Thr Thr
    130             135             140

AAT GCG AGC CTG CTG ACG AAG CTG CAG GCA CAG AAC CAG TGG CTG CAG   480
Asn Ala Ser Leu Leu Thr Lys Leu Gln Ala Gln Asn Gln Trp Leu Gln
145             150             155             160

GAC ATG ACA ACT CAT CTC ATT CTG AGA TCT TTT AAA GAA TTC CTG CAG   528
Asp Met Thr Thr His Leu Ile Leu Arg Ser Phe Lys Glu Phe Leu Gln
                165             170             175

TCC TCC CTG CGT GCT CTG CGT CAG ATG TAATGATAG                     564
Ser Ser Leu Arg Ala Leu Arg Gln Met
        180             185
```

( 2 ) INFORMATION FOR SEQ ID NO:2:

( i ) SEQUENCE CHARACTERISTICS:
      ( A ) LENGTH: 185 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

```
Ala Pro Val Pro Pro Gly Glu Asp Ser Lys Asp Val Ala Ala Pro His
 1               5              10                  15

Arg Gln Pro Leu Thr Ser Ser Glu Arg Ile Asp Lys Gln Ile Arg Tyr
            20                  25                  30

Ile Leu Asp Gly Ile Ser Ala Leu Arg Lys Glu Thr Cys Asn Lys Ser
            35                  40                  45

Asn Met Cys Glu Ser Ser Lys Glu Ala Leu Ala Glu Asn Asn Leu Asn
    50                  55                  60

Leu Pro Lys Met Ala Glu Lys Asp Gly Cys Phe Gln Ser Gly Phe Asn
65                  70                  75                  80

Glu Glu Thr Cys Leu Val Lys Ile Ile Thr Gly Leu Leu Glu Phe Glu
                85                  90                  95

Val Tyr Leu Glu Tyr Leu Gln Asn Arg Phe Glu Ser Ser Glu Glu Gln
            100                 105                 110

Ala Arg Ala Val Gln Met Ser Thr Lys Val Leu Ile Gln Phe Leu Gln
        115                 120                 125

Lys Lys Ala Lys Asn Leu Asp Ala Ile Thr Thr Pro Asp Pro Thr Thr
    130                 135                 140

Asn Ala Ser Leu Leu Thr Lys Leu Gln Ala Gln Asn Gln Trp Leu Gln
145                 150                 155                 160

Asp Met Thr Thr His Leu Ile Leu Arg Ser Phe Lys Glu Phe Leu Gln
                165                 170                 175

Ser Ser Leu Arg Ala Leu Arg Gln Met
        180                 185
```

( 2 ) INFORMATION FOR SEQ ID NO:3:

( i ) SEQUENCE CHARACTERISTICS:
      ( A ) LENGTH: 564 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: CDS
    ( B ) LOCATION: 1..558

( i x ) FEATURE:
    ( A ) NAME/KEY: matpeptide
    ( B ) LOCATION: 1..555

( x i ) SEQUENCE DESCRIPTION: SEQ ID NO:3:

```
GCT CCG GTT CCG CCA GGA GAA GAT TCC AAA GAT GTA GCC GCC CCA CAC   048
Ala Pro Val Pro Pro Gly Glu Asp Ser Lys Asp Val Ala Ala Pro His
 1               5                  10                  15

AGA CAG CCG CTC ACC TCT TCA GAA CGA ATC GAT AAA CAA ATT CGG TAC   096
Arg Gln Pro Leu Thr Ser Ser Glu Arg Ile Asp Lys Gln Ile Arg Tyr
            20                  25                  30

ATC CTC GAC GGG ATA TCA GCG CTG AGA AAA GAG ACC TGT AAC AAG AGT   144
Ile Leu Asp Gly Ile Ser Ala Leu Arg Lys Glu Thr Cys Asn Lys Ser
        35                  40                  45

AAC ATG TGT GAA AGC AGT AAA GAA GCA CTG GCA GAA AAC AAC CTG AAC   192
Asn Met Cys Glu Ser Ser Lys Glu Ala Leu Ala Glu Asn Asn Leu Asn
    50                  55                  60

CTT CCG AAG ATG GCT GAA AAA GAT GGA TGT TTT CAA TCT GGA TTC AAT   240
Leu Pro Lys Met Ala Glu Lys Asp Gly Cys Phe Gln Ser Gly Phe Asn
 65                 70                  75                  80

GAG GAA ACT TGT CTG GTG AAA ATC ATC ACA GGC CTT TTG GAA TTT GAG   288
Glu Glu Thr Cys Leu Val Lys Ile Ile Thr Gly Leu Leu Glu Phe Glu
                85                  90                  95

GTA TAC CTA GAG TAC CTC CAG AAC AGA TTT GAG AGT AGT GAG GAA CAA   336
Val Tyr Leu Glu Tyr Leu Gln Asn Arg Phe Glu Ser Ser Glu Glu Gln
            100                 105                 110

GCG AGA GCT GTC CAG ATG TCG ACC AAA GTC CTG ATC CAG TTT CTG CAG   384
Ala Arg Ala Val Gln Met Ser Thr Lys Val Leu Ile Gln Phe Leu Gln
        115                 120                 125

AAA AAG GCA AAA AAT CTA GAT GCA ATA ACC ACC CCG GAT CCA ACC ACA   432
Lys Lys Ala Lys Asn Leu Asp Ala Ile Thr Thr Pro Asp Pro Thr Thr
130                 135                 140

AAT GCG AGC CTG CTG ACG AAG CTG CAG GCA CAG AAC CAG TGG CTG CAG   480
Asn Ala Ser Leu Leu Thr Lys Leu Gln Ala Gln Asn Gln Trp Leu Gln
145                 150                 155                 160

GAC ATG ACA ACT CAT CTC ATT CTG AGA TCT TTG AAA GAA TTC CTG CAG   528
Asp Met Thr Thr His Leu Ile Leu Arg Ser Leu Lys Glu Phe Leu Gln
                165                 170                 175

TCC TCC CTG CGT GCT CTG CGT CAG ATG TAATGATAG                     564
Ser Ser Leu Arg Ala Leu Arg Gln Met
            180                 185
```

( 2 ) INFORMATION FOR SEQ ID NO:4:

( i ) SEQUENCE CHARACTERISTICS:
        ( A ) LENGTH: 185 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Ala Pro Val Pro Pro Gly Glu Asp Ser Lys Asp Val Ala Ala Pro His
 1               5                  10                  15

Arg Gln Pro Leu Thr Ser Ser Glu Arg Ile Asp Lys Gln Ile Arg Tyr
            20                  25                  30
```

| | | | | | | | | | | | | | | |
|---|---|---|---|---|---|---|---|---|---|---|---|---|---|---|
| Ile | Leu | Asp | Gly | Ile | Ser | Ala | Leu | Arg | Lys | Glu | Thr | Cys | Asn | Lys | Ser |
| | | 35 | | | | | 40 | | | | | 45 | | | |
| Asn | Met | Cys | Glu | Ser | Ser | Lys | Glu | Ala | Leu | Ala | Glu | Asn | Asn | Leu | Asn |
| | 50 | | | | | 55 | | | | | 60 | | | | |
| Leu | Pro | Lys | Met | Ala | Glu | Lys | Asp | Gly | Cys | Phe | Gln | Ser | Gly | Phe | Asn |
| 65 | | | | | 70 | | | | | 75 | | | | | 80 |
| Glu | Glu | Thr | Cys | Leu | Val | Lys | Ile | Ile | Thr | Gly | Leu | Leu | Glu | Phe | Glu |
| | | | | 85 | | | | | 90 | | | | | 95 | |
| Val | Tyr | Leu | Glu | Tyr | Leu | Gln | Asn | Arg | Phe | Glu | Ser | Ser | Glu | Glu | Gln |
| | | | 100 | | | | | 105 | | | | | 110 | | |
| Ala | Arg | Ala | Val | Gln | Met | Ser | Thr | Lys | Val | Leu | Ile | Gln | Phe | Leu | Gln |
| | | 115 | | | | | 120 | | | | | 125 | | | |
| Lys | Lys | Ala | Lys | Asn | Leu | Asp | Ala | Ile | Thr | Thr | Pro | Asp | Pro | Thr | Thr |
| | 130 | | | | | 135 | | | | | 140 | | | | |
| Asn | Ala | Ser | Leu | Leu | Thr | Lys | Leu | Gln | Ala | Gln | Asn | Gln | Trp | Leu | Gln |
| 145 | | | | | 150 | | | | | 155 | | | | | 160 |
| Asp | Met | Thr | Thr | His | Leu | Ile | Leu | Arg | Ser | Leu | Lys | Glu | Phe | Leu | Gln |
| | | | | 165 | | | | | 170 | | | | | 175 | |
| Ser | Ser | Leu | Arg | Ala | Leu | Arg | Gln | Met | | | | | | | |
| | | | 180 | | | | | 185 | | | | | | | |

( 2 ) INFORMATION FOR SEQ ID NO:5:

( i ) SEQUENCE CHARACTERISTICS:
        ( A ) LENGTH: 564 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..558

( i x ) FEATURE:
        ( A ) NAME/KEY: matpeptide
        ( B ) LOCATION: 1..555

( x i ) SEQUENCE DESCRIPTION: SEQ ID NO:5:

| | | | | | | | | | | | | | | | |
|---|---|---|---|---|---|---|---|---|---|---|---|---|---|---|---|
| GCT | CCG | GTT | CCG | CCA | GGA | GAA | GAT | TCC | AAA | GAT | GTA | GCC | GCC | CCA | CAC | 048 |
| Ala | Pro | Val | Pro | Pro | Gly | Glu | Asp | Ser | Lys | Asp | Val | Ala | Ala | Pro | His |
| 1 | | | | 5 | | | | | 10 | | | | | 15 | |
| AGA | CAG | CCG | CTC | ACC | TCT | TCA | GAA | CGA | ATC | GAT | AAA | CAA | ATT | CGG | TAC | 096 |
| Arg | Gln | Pro | Leu | Thr | Ser | Ser | Glu | Arg | Ile | Asp | Lys | Gln | Ile | Arg | Tyr |
| | | | 20 | | | | | 25 | | | | | 30 | | |
| ATC | CTC | GAC | GGG | ATA | TCA | GCG | CTG | AGA | AAA | GAG | ACC | TGT | AAC | AAG | AGT | 144 |
| Ile | Leu | Asp | Gly | Ile | Ser | Ala | Leu | Arg | Lys | Glu | Thr | Cys | Asn | Lys | Ser |
| | | 35 | | | | | 40 | | | | | 45 | | | |
| AAC | ATG | TGT | GAA | AGC | AGT | AAA | GAA | GCA | CTG | GCA | GAA | AAC | AAC | CTG | AAC | 192 |
| Asn | Met | Cys | Glu | Ser | Ser | Lys | Glu | Ala | Leu | Ala | Glu | Asn | Asn | Leu | Asn |
| | 50 | | | | | 55 | | | | | 60 | | | | |
| CTT | CCG | AAG | ATG | GCT | GAA | AAA | GAT | GGA | TGT | TTT | CAA | TCT | GGA | TTC | AAT | 240 |
| Leu | Pro | Lys | Met | Ala | Glu | Lys | Asp | Gly | Cys | Phe | Gln | Ser | Gly | Phe | Asn |
| 65 | | | | | 70 | | | | | 75 | | | | | 80 |
| GAG | GAA | ACT | TGT | CTG | GTG | AAA | ATC | ATC | ACA | GGC | CTT | TTG | GAA | TTT | GAG | 288 |
| Glu | Glu | Thr | Cys | Leu | Val | Lys | Ile | Ile | Thr | Gly | Leu | Leu | Glu | Phe | Glu |
| | | | | 85 | | | | | 90 | | | | | 95 | |
| GTA | TAC | CTA | GAG | TAC | CTC | CAG | AAC | AGA | TTT | GAG | AGT | AGT | GAG | GAA | CAA | 336 |
| Val | Tyr | Leu | Glu | Tyr | Leu | Gln | Asn | Arg | Phe | Glu | Ser | Ser | Glu | Glu | Gln |
| | | | 100 | | | | | 105 | | | | | 110 | | |

```
GCG  AGA  GCT  GTC  CAG  ATG  TCG  ACC  AAA  GTC  CTG  ATC  CAG  TTT  CTG  CAG    384
Ala  Arg  Ala  Val  Gln  Met  Ser  Thr  Lys  Val  Leu  Ile  Gln  Phe  Leu  Gln
          115                      120                      125

AAA  AAG  GCA  AAA  AAT  CTA  GAT  GCA  ATA  ACC  ACC  CCG  GAT  CCA  ACC  ACA    432
Lys  Lys  Ala  Lys  Asn  Leu  Asp  Ala  Ile  Thr  Thr  Pro  Asp  Pro  Thr  Thr
     130                      135                      140

AAT  GCG  AGC  CTG  CTG  ACG  AAG  CTG  CAG  GCA  CAG  AAC  CAG  TGG  CTG  CAG    480
Asn  Ala  Ser  Leu  Leu  Thr  Lys  Leu  Gln  Ala  Gln  Asn  Gln  Trp  Leu  Gln
145                      150                      155                      160

GAC  ATG  ACA  ACT  CAT  CTC  ATT  CTG  AGA  TCT  TTT  AAA  GAA  TTC  ATG  CAG    528
Asp  Met  Thr  Thr  His  Leu  Ile  Leu  Arg  Ser  Phe  Lys  Glu  Phe  Met  Gln
               165                      170                      175

TCC  TCC  CTG  CGT  GCT  CTG  CGT  CAG  ATG  TAATGATAG                             564
Ser  Ser  Leu  Arg  Ala  Leu  Arg  Gln  Met
          180                      185
```

( 2 ) INFORMATION FOR SEQ ID NO:6:

( i ) SEQUENCE CHARACTERISTICS:
        ( A ) LENGTH: 185 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Ala  Pro  Val  Pro  Pro  Gly  Glu  Asp  Ser  Lys  Asp  Val  Ala  Ala  Pro  His
 1                   5                        10                       15

Arg  Gln  Pro  Leu  Thr  Ser  Ser  Glu  Arg  Ile  Asp  Lys  Gln  Ile  Arg  Tyr
               20                       25                       30

Ile  Leu  Asp  Gly  Ile  Ser  Ala  Leu  Arg  Lys  Glu  Thr  Cys  Asn  Lys  Ser
          35                       40                       45

Asn  Met  Cys  Glu  Ser  Ser  Lys  Glu  Ala  Leu  Ala  Glu  Asn  Asn  Leu  Asn
     50                       55                       60

Leu  Pro  Lys  Met  Ala  Glu  Lys  Asp  Gly  Cys  Phe  Gln  Ser  Gly  Phe  Asn
65                       70                       75                       80

Glu  Glu  Thr  Cys  Leu  Val  Lys  Ile  Ile  Thr  Gly  Leu  Leu  Glu  Phe  Glu
               85                       90                       95

Val  Tyr  Leu  Glu  Tyr  Leu  Gln  Asn  Arg  Phe  Glu  Ser  Ser  Glu  Glu  Gln
               100                      105                      110

Ala  Arg  Ala  Val  Gln  Met  Ser  Thr  Lys  Val  Leu  Ile  Gln  Phe  Leu  Gln
          115                      120                      125

Lys  Lys  Ala  Lys  Asn  Leu  Asp  Ala  Ile  Thr  Thr  Pro  Asp  Pro  Thr  Thr
     130                      135                      140

Asn  Ala  Ser  Leu  Leu  Thr  Lys  Leu  Gln  Ala  Gln  Asn  Gln  Trp  Leu  Gln
145                      150                      155                      160

Asp  Met  Thr  Thr  His  Leu  Ile  Leu  Arg  Ser  Phe  Lys  Glu  Phe  Met  Gln
               165                      170                      175

Ser  Ser  Leu  Arg  Ala  Leu  Arg  Gln  Met
          180                      185
```

( 2 ) INFORMATION FOR SEQ ID NO:7:

( i ) SEQUENCE CHARACTERISTICS:
        ( A ) LENGTH: 564 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: CDS
    ( B ) LOCATION: 1..558

( i x ) FEATURE:
    ( A ) NAME/KEY: matpeptide
    ( B ) LOCATION: 1..555

( x i ) SEQUENCE DESCRIPTION: SEQ ID NO:7:

```
GCT  CCG  GTT  CCG  CCA  GGA  GAA  GAT  TCC  AAA  GAT  GTA  GCC  GCC  CCA  CAC   048
Ala  Pro  Val  Pro  Pro  Gly  Glu  Asp  Ser  Lys  Asp  Val  Ala  Ala  Pro  His
 1              5                        10                       15

AGA  CAG  CCG  CTC  ACC  TCT  TCA  GAA  CGA  ATC  GAT  AAA  CAA  ATT  CGG  TAC   096
Arg  Gln  Pro  Leu  Thr  Ser  Ser  Glu  Arg  Ile  Asp  Lys  Gln  Ile  Arg  Tyr
              20                        25                       30

ATC  CTC  GAC  GGG  ATA  TCA  GCG  CTG  AGA  AAA  GAG  ACC  TGT  AAC  AAG  AGT   144
Ile  Leu  Asp  Gly  Ile  Ser  Ala  Leu  Arg  Lys  Glu  Thr  Cys  Asn  Lys  Ser
              35                        40                       45

AAC  ATG  TGT  GAA  AGC  AGT  AAA  GAA  GCA  CTG  GCA  GAA  AAC  AAC  CTG  AAC   192
Asn  Met  Cys  Glu  Ser  Ser  Lys  Glu  Ala  Leu  Ala  Glu  Asn  Asn  Leu  Asn
      50                        55                       60

CTT  CCG  AAG  ATG  GCT  GAA  AAA  GAT  GGA  TGT  TTT  CAA  TCT  GGA  TTC  AAT   240
Leu  Pro  Lys  Met  Ala  Glu  Lys  Asp  Gly  Cys  Phe  Gln  Ser  Gly  Phe  Asn
 65                        70                       75                       80

GAG  GAA  ACT  TGT  CTG  GTG  AAA  ATC  ATC  ACA  GGC  CTT  TTG  GAA  TTT  GAG   288
Glu  Glu  Thr  Cys  Leu  Val  Lys  Ile  Ile  Thr  Gly  Leu  Leu  Glu  Phe  Glu
                     85                       90                       95

GTA  TAC  CTA  GAG  TAC  CTC  CAG  AAC  AGA  TTT  GAG  AGT  AGT  GAG  GAA  CAA   336
Val  Tyr  Leu  Glu  Tyr  Leu  Gln  Asn  Arg  Phe  Glu  Ser  Ser  Glu  Glu  Gln
                    100                      105                      110

GCG  AGA  GCT  GTC  CAG  ATG  TCG  ACC  AAA  GTC  CTG  ATC  CAG  TTT  CTG  CAG   384
Ala  Arg  Ala  Val  Gln  Met  Ser  Thr  Lys  Val  Leu  Ile  Gln  Phe  Leu  Gln
                    115                      120                      125

AAA  AAG  GCA  AAA  AAT  CTA  GAT  GCA  ATA  ACC  ACC  CCG  GAT  CCA  ACC  ACA   432
Lys  Lys  Ala  Lys  Asn  Leu  Asp  Ala  Ile  Thr  Thr  Pro  Asp  Pro  Thr  Thr
     130                      135                      140

AAT  GCG  AGC  CTG  CTG  ACG  AAG  CTG  CAG  GCA  CAG  AAC  CAG  TGG  CTG  CAG   480
Asn  Ala  Ser  Leu  Leu  Thr  Lys  Leu  Gln  Ala  Gln  Asn  Gln  Trp  Leu  Gln
145                      150                      155                      160

GAC  ATG  ACA  ACT  CAT  CTC  ATT  CTG  AGA  TCT  TTG  AAA  GAA  TTC  ATG  CAG   528
Asp  Met  Thr  Thr  His  Leu  Ile  Leu  Arg  Ser  Leu  Lys  Glu  Phe  Met  Gln
                    165                      170                      175

TCC  TCC  CTG  CGT  GCT  CTG  CGT  CAG  ATG  TAATGATAG                           564
Ser  Ser  Leu  Arg  Ala  Leu  Arg  Gln  Met
                    180                      185
```

( 2 ) INFORMATION FOR SEQ ID NO:8:

( i ) SEQUENCE CHARACTERISTICS:
        ( A ) LENGTH: 185 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Ala  Pro  Val  Pro  Pro  Gly  Glu  Asp  Ser  Lys  Asp  Val  Ala  Ala  Pro  His
 1              5                        10                       15

Arg  Gln  Pro  Leu  Thr  Ser  Ser  Glu  Arg  Ile  Asp  Lys  Gln  Ile  Arg  Tyr
              20                        25                       30

Ile  Leu  Asp  Gly  Ile  Ser  Ala  Leu  Arg  Lys  Glu  Thr  Cys  Asn  Lys  Ser
              35                        40                       45

Asn  Met  Cys  Glu  Ser  Ser  Lys  Glu  Ala  Leu  Ala  Glu  Asn  Asn  Leu  Asn
```

```
                50                          55                          60
Leu   Pro   Lys   Met   Ala   Glu   Lys   Asp   Gly   Cys   Phe   Gln   Ser   Gly   Phe   Asn
 65                      70                            75                            80

Glu   Glu   Thr   Cys   Leu   Val   Lys   Ile   Ile   Thr   Gly   Leu   Leu   Glu   Phe   Glu
                         85                            90                            95

Val   Tyr   Leu   Glu   Tyr   Leu   Gln   Asn   Arg   Phe   Glu   Ser   Ser   Glu   Glu   Gln
                  100                         105                         110

Ala   Arg   Ala   Val   Gln   Met   Ser   Thr   Lys   Val   Leu   Ile   Gln   Phe   Leu   Gln
            115                         120                         125

Lys   Lys   Ala   Lys   Asn   Leu   Asp   Ala   Ile   Thr   Thr   Pro   Asp   Pro   Thr   Thr
      130                         135                         140

Asn   Ala   Ser   Leu   Leu   Thr   Lys   Leu   Gln   Ala   Gln   Asn   Gln   Trp   Leu   Gln
145                         150                         155                         160

Asp   Met   Thr   Thr   His   Leu   Ile   Leu   Arg   Ser   Leu   Lys   Glu   Phe   Met   Gln
                  165                         170                         175

Ser   Ser   Leu   Arg   Ala   Leu   Arg   Gln   Met
                  180                         185
```

( 2 ) INFORMATION FOR SEQ ID NO:9:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

GATCCTAAGT AGTAGGTACC AAGCTTGAC                                                 0 2 9

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

GTGAAGCTTG GTACCTACTA CTTAA                                                       0 2 5

( 2 ) INFORMATION FOR SEQ ID NO:11:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

GATCTTTTAA GGAGTTCCTG CAGTCTAGCC TGAGAGCTCT TCGGCAAATG TCAGACTCTG      0 6 0

TGCC                                                                                                                    064

(2) INFORMATION FOR SEQ ID NO:12:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

TGTTGGTCCT GTTGGTCCTG CTGGTGCTTT TGGCCCAAGA GGTCTCGCTG GCCCACAAGG   060

TCCAC                                                                                                                   065

(2) INFORMATION FOR SEQ ID NO:13:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

GTGGACCTTG TGGGCCAGCG AGACCTCTTG GGCCAAAAGC ACCAGCAGGA CCAACAGGAC   060

C                                                                                                                       061

(2) INFORMATION FOR SEQ ID NO:14:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:14:

AACAGGCACA GAATCTGACA TTTGCCGAAG AGCTCTCAGG CTAGACTGCA GGAACTCCTT   060

AAAA                                                                                                                    064

(2) INFORMATION FOR SEQ ID NO:15:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:15:

```
GATCTTTTAA  GGAGTTCCTG  CAGTCTAGCC  TGAGAGCTCT  TCGGCAAATG  TCAGACTCTG   60

TGCCTGAAGG  TCCTGTTGGT  CCTGCTGGTG  CTTTTGGCCC  AAGAGGTCTC  GCTGGCCCAC  120

AAGCTGCAC                                                               129
```

( 2 ) INFORMATION FOR SEQ ID NO:16:

( i ) SEQUENCE CHARACTERISTICS:
        ( A ) LENGTH: 125 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:16:

```
CTCGACCTTG  TGGGCCAGCG  AGACCTCTTG  GGCCAAAGGC  ACCAGCAGGA  CCAACAGGAC   60

CAACAGGCAC  AGAGTCTGAC  ATTTGCCGAA  GAGCTCTCAG  GCTAGACTGC  AGGAACTCCT  120

TAAAA                                                                   125
```

( 2 ) INFORMATION FOR SEQ ID NO:17:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:17:

```
Phe  Lys  Asp  Phe  Leu  Gln  Ser  Ser  Leu  Arg  Ala  Leu  Arg  Gln  Met
 1              5                        10                         15
```

( 2 ) INFORMATION FOR SEQ ID NO:18:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:18:

```
Cys  Lys  Glu  Phe  Leu  Gln  Ser  Ser  Leu  Arg  Ala  Leu  Arg  Gln  Met
 1              5                        10                         15
```

( 2 ) INFORMATION FOR SEQ ID NO:19:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:19:

```
Leu Lys Glu Phe Leu Gln Ser Ser Leu Arg Ala Leu Arg Gln Met
 1               5                  10                  15
```

(2) INFORMATION FOR SEQ ID NO:20:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:20:

```
Phe Gln Glu Phe Leu Gln Ser Ser Leu Arg Ala Leu Arg Gln Met
 1               5                  10                  15
```

(2) INFORMATION FOR SEQ ID NO:21:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:21:

```
Phe Lys Asp Phe Leu Gln Ser Ser Leu Arg Ala Leu Arg Gln Met
 1               5                  10                  15
```

(2) INFORMATION FOR SEQ ID NO:22:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:22:

```
Phe Lys Glu Val Leu Gln Ser Ser Leu Arg Ala Leu Arg Gln Met
 1               5                  10                  15
```

(2) INFORMATION FOR SEQ ID NO:23:

```
    Phe  Lys  Glu  Phe  Leu  Gln  Ser  Arg  Leu  Arg  Ala  Leu  Arg  Gln  Met
    1                   5                        10                        15
```

( 2 ) INFORMATION FOR SEQ ID NO:27:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:27:

```
    Phe  Lys  Glu  Phe  Leu  Gln  Ser  Ser  Arg  Arg  Ala  Leu  Arg  Gln  Met
    1                   5                        10                        15
```

( 2 ) INFORMATION FOR SEQ ID NO:28:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:28:

```
    Phe  Lys  Glu  Phe  Leu  Gln  Ser  Ser  Leu  Lys  Ala  Leu  Arg  Gln  Met
    1                   5                        10                        15
```

( 2 ) INFORMATION FOR SEQ ID NO:29:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:29:

```
    Phe  Lys  Glu  Phe  Leu  Gln  Ser  Ser  Leu  Arg  Asp  Leu  Arg  Gln  Met
    1                   5                        10                        15
```

( 2 ) INFORMATION FOR SEQ ID NO:30:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO (i) SEQUENCE CHARACTERISTICS:
  (A) LENGTH: 15 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:23:

Phe Lys Glu Phe Met Gln Ser Ser Leu Arg Ala Leu Arg Gln Met
1               5                   10                  15

(2) INFORMATION FOR SEQ ID NO:24:

(i) SEQUENCE CHARACTERISTICS:
  (A) LENGTH: 15 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:24:

Phe Lys Glu Phe Leu Lys Ser Ser Leu Arg Ala Leu Arg Gln Met
1               5                   10                  15

(2) INFORMATION FOR SEQ ID NO:25:

(i) SEQUENCE CHARACTERISTICS:
  (A) LENGTH: 15 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:25:

Phe Lys Glu Phe Leu Gln Pro Ser Leu Arg Ala Leu Arg Gln Met
1               5                   10                  15

(2) INFORMATION FOR SEQ ID NO:26:

(i) SEQUENCE CHARACTERISTICS:
  (A) LENGTH: 15 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:26:

(i v) ANTI-SENSE: NO (v) FRAGMENT TYPE: C-terminal (x i) SEQUENCE DESCRIPTION: SEQ ID NO:30:

```
Phe Lys Glu Phe Leu Gln Ser Ser Leu Arg Thr Leu Arg Gln Met
 1               5                  10                  15
```

(2) INFORMATION FOR SEQ ID NO:31:

(i) SEQUENCE CHARACTERISTICS:
        (A) LENGTH: 15 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: C-terminal (x i) SEQUENCE DESCRIPTION: SEQ ID NO:31:

```
Phe Lys Glu Phe Leu Gln Ser Ser Leu Arg Ala Val Arg Gln Met
 1               5                  10                  15
```

(2) INFORMATION FOR SEQ ID NO:32:

(i) SEQUENCE CHARACTERISTICS:
        (A) LENGTH: 15 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: C-terminal (x i) SEQUENCE DESCRIPTION: SEQ ID NO:32:

```
Phe Lys Glu Phe Leu Gln Ser Ser Leu Arg Ala Ile Arg Gln Met
 1               5                  10                  15
```

(2) INFORMATION FOR SEQ ID NO:33:

(i) SEQUENCE CHARACTERISTICS:
        (A) LENGTH: 15 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: C-terminal (x i) SEQUENCE DESCRIPTION: SEQ ID NO:33:

```
Phe Lys Glu Phe Leu Gln Ser Ser Leu Arg Ala Leu Trp Gln Met
 1               5                  10                  15
```

(2) INFORMATION FOR SEQ ID NO:34:

(i) SEQUENCE CHARACTERISTICS:
        (A) LENGTH: 15 amino acids
        (B) TYPE: amino acid

```
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:34:

Phe  Lys  Glu  Phe  Leu  Gln  Ser  Ser  Leu  Arg  Ala  Leu  Arg  Pro  Met
     1              5                        10                         15

( 2 ) INFORMATION FOR SEQ ID NO:35:

( i ) SEQUENCE CHARACTERISTICS:
            ( A ) LENGTH: 15 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:35:

Phe  Lys  Glu  Phe  Leu  Gln  Ser  Ser  Leu  Arg  Ala  Leu  Arg  Gln  Ile
     1              5                        10                         15
```